United States Patent [19]

Stone et al.

[11] Patent Number: 5,372,607
[45] Date of Patent: Dec. 13, 1994

[54] METHOD AND APPARATUS FOR MONITORING PACEMAKER INTERVALS

[75] Inventors: Karen A. Stone, White Bear Lake; Richard M. Powell, Bloomington; Michael R. Tollinger, Andover; Gary Berg, Edina, all of Minn.

[73] Assignee: Medtronic, Inc., Minneapolis, Minn.

[21] Appl. No.: 81,721

[22] Filed: Jun. 23, 1993

[51] Int. Cl.$^5$ ............................................. A61N 1/365
[52] U.S. Cl. .......................................... 607/30; 607/22
[58] Field of Search ...................... 607/17, 19, 22, 27

[56] References Cited

U.S. PATENT DOCUMENTS

| | | | |
|---|---|---|---|
| 4,060,090 | 11/1977 | Lin et al. | 128/419 |
| 4,257,423 | 3/1981 | McDonald et al. | 128/419 |
| 4,374,382 | 2/1983 | Markowitz | 340/870.01 |
| 4,379,459 | 4/1983 | Stein | 128/419 |
| 4,421,116 | 12/1983 | Markowitz | 128/419 |
| 4,467,807 | 8/1984 | Bornzin | 128/419 |
| 4,485,813 | 12/1984 | Anderson et al. | 128/675 |
| 4,556,063 | 12/1985 | Thompson et al. | 128/419 |
| 4,750,495 | 6/1988 | Moore et al. | 128/419 |
| 4,807,629 | 2/1989 | Baudino et al. | 128/419 |
| 4,856,522 | 8/1989 | Hansen | 607/17 |
| 4,867,160 | 9/1989 | Schaldach | 128/419 |
| 4,867,162 | 9/1989 | Schaldach | 607/22 |
| 4,940,093 | 7/1990 | Mann et al. | 607/19 |
| 5,052,388 | 10/1991 | Sivula et al. | 128/419 |
| 5,127,404 | 7/1992 | Wybomy et al. | 128/419 |
| 5,133,349 | 7/1992 | Heinze | 607/22 |

OTHER PUBLICATIONS

"Multidimensional curve fitting program for biological data", Computer Programs in Biomedicine 18 (1984) pp. 259–264.

"Physiological Relationship Between AV Interval and Heart Rate in Healthy Subjects: Applications to Dual Chamber Pacing", PACE, vol. 9, pp. 1032–1039.

"Effect of rate-adapting atrioventricular delay on stroke volume and cardiac output during atrial synchronous pacing", Can J Cardiol, vol. 6, No. 10, Dec. 1990, pp. 445–452.

"Intrinsic Conduction Maximizes Cardiopulmonary Performance in Patients with Dual Chamber Pacemakers", PACE, vol. 14, Nov. 1991, pp. 1787–1791.

Primary Examiner—William E. Kamm
Attorney, Agent, or Firm—Harold R. Patton

[57] ABSTRACT

A method and apparatus for optimizing the performance of a rate-responsive cardiac pacemaker. A pacemaker is provided which is capable of obtaining and storing information about a patient's cardiac function and about a pacemaker's operation during a brief exercise interval. The data collected includes information about the number of cardiac events during each two-second interval of the exercise, as well as the percentage of paced events during each two-second interval. Data reflecting the output of the pacemaker's activity sensor output is also collected for each two second interval of the test. In addition, AV interval data for each cardiac cycle during the test is collected, this data being distinguished according to whether it reflects atrial-pace-to-ventricular-sense or atrial-sense-to-ventricular-sense AV intervals. The disclosed pacemaker is operable in conjunction with an external programming/processing unit, which receives the stored data after the exercise test is concluded. The data is processed and presented on the programmer screen in a manner which enables the clinician to readily assimilate it and observe the effects of hypothetical changes in rate-response programming in the pacemaker. Additionally, the clinician is able to observe the programmed AV rate adaption profiles in conjunction with the patient's actual AV performance, and compare this data with an AV profile from a typical healthy heart.

28 Claims, 7 Drawing Sheets

METHOD AND APPARATUS FOR MONITORING PACEMAKER INTERVALS

FIELD OF THE INVENTION

This invention relates to the field of implantable medical devices, and more particularly relates to cardiac pacemakers which respond to a patient's metabolic demand for oxygenated blood and vary the pacing rate in accordance therewith.

BACKGROUND OF THE INVENTION

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiologically-based signals, such as signals from sensors for measuring the pressure inside the patient's ventricle or for measuring the level of the patient's physical activity. In recent years, pacemakers which measure the metabolic demand for oxygen and vary the pacing rate in response thereto have become widely available. Perhaps the most popularly employed method for measuring the need for oxygenated blood is to measure the physical activity of the patient by means of a piezoelectric transducer. A piezoelectric crystal for activity sensing is typically fixed to the pacemaker shield and generates an electrical signal in response to deflections of the pacemaker shield caused by patient activity. Piezoelectric, microphone-like sensors are widely used in rate-responsive pacemakers because they are relatively inexpensive, their manufactured yield is high, and they transduce the acoustic energy of patients' motion in a highly reliable manner. A pacemaker employing a piezoelectric activity sensor is disclosed in U.S. Pat. No. 4,485,813 issued to Anderson et al., which patent is hereby incorporated by reference herein in its entirety.

Although piezoelectric activity sensors are common, there are other methods of monitoring a patient's metabolic demand for oxygenated blood. For example, blood oxygen saturation may be measured directly, as disclosed in U.S. Pat. No. 4,467,807 issued to Bornzin, U.S. Pat. No. 4,807,629 issued to Baudino et al., and in U.S. Pat. No. 4,750,495 issued to Brumwell et al. Alternatively, pacing rate can be varied as a function of a measured value representative of stroke volume, as described in U.S. Pat. No. 4,867,160 to Schaldach.

Other physiologic conditions that can be used as an indication of a patient's metabolic demand for oxygenated blood include: right ventricular blood pressure and the change of right ventricular blood pressure over time, venous blood temperature, respiration rate, minute ventilation, and various pre- and post-systolic time intervals. Such conditions can be measured, for example, by impedance or pressure sensing within the right ventricle of the heart.

In typical prior art rate-responsive pacemakers having some type of activity sensor, the pacing rate is varied according to the output from the sensor. Usually, the pacing rate is variable between a predetermined maximum and minimum level, which may be selectable by a physician from among a plurality of programmable upper and lower rate limit settings. When the activity sensor output indicates that the patient's activity level has increased, the pacing rate is increased accordingly. As long as patient activity continues to be indicated, the pacing rate is periodically increased by some incremental amount, until the computed activity target rate or the programmed upper rate limit is reached. When patient activity ceases, the pacing rate is gradually reduced, until the programmed lower rate limit is reached.

In one prior art technique employing a piezoelectric, microphone-like sensor for transducing patient activity, the raw electrical signal output from the sensor is applied to an AC-coupled system which bandpass filters the signal prior to being applied to pacemaker rate-setting logic. This arrangement is disclosed in U.S. Pat. No. 5,052,388 to Sivula et al., assigned by the assignee of the present invention and incorporated herein by reference in its entirety. According to the Sivula et al. patent, peaks in the bandpass filtered sensor signal which exceed a predetermined threshold are interpreted by the rate-setting logic as an indication of patient activity of sufficient magnitude that an increase in the pacing rate may be warranted. The predetermined threshold, which may also be selectable by a physician from one of a plurality of programmable settings, is intended to screen out background "noise" in the sensor output signal indicative of low amplitude patient motion. Each occurrence of a peak in the bandpass-filtered sensor signal which exceeds the threshold level is known as a "sensor detect". A sum of sensor detects is computed over some period of time; for example, the number of sensor detects may be determined every two seconds. If, at the end of that period, the number of sensor detects exceeds some predetermined value, the rate-setting logic interprets this as an indication that the pacing rate should be incrementally increased.

In order to minimize patient problems and to prolong or extend the useful life of an implanted pacemaker, it has become common practice to provide programmable pacemaker parameters in order to permit the physician or clinician to adjust and fine-tune the operation of the pacemaker to match or optimize the pacing therapy to the patient's physiologic requirements. For example, the physician may adjust the stimulating pulse energy settings to maximize the pacemaker battery longevity while ensuring an adequate safety margin. Additionally, the physician may adjust the sensing threshold to ensure adequate sensing of intrinsic depolarizations of cardiac tissue, while preventing or minimizing oversensing of unwanted events such as myopotential interference or electromagnetic interference (EMI).

There are typically a number of programmable parameters associated with the rate-responsive operation of pacemakers. For the rate-responsive pacemaker described in the above-referenced Sivula et al. patent, for example, an upper rate limit, lower rate limit, and one of a plurality of rate response settings must be selected. The rate response setting is used to determine the increment to pacing rate as a function of sensor output, i.e., the slope of the function correlating the pacing rate curve in response to detected patient activity.

Similarly, other pacemakers, such as Medtronic, Inc.'s Activitrax II Models 8412–14, Medtronic, Inc.'s Legend Models 8416–18, Siemens, Elema AB's Sensolog 703, Cook Pacemaker Corp.'s Sensor Model Kelvin 500, Telectronics' Meta MV Model 1202, Cordis Pacing Systems' Prism CL Model 450A, Intermedics, Inc.'s Nova MR, and Vitatron Medical B.V.'s Diamond pacemakers have incorporated the programmability feature of various variables associated with their rate-responsiveness.

The Sensolog 703 pacemaker is a single-chamber activity sensing, rate modulated, multi-programmable pulse generator whose main programmable variables include pacing mode, sensor states, minimum and maximum pacing rates, recovery time, and responsiveness. The responsiveness of the pulse generator is determined by two calibration points corresponding to two levels of exercise called "low work" (LW) and "high work" (HW). During the adjustment procedure, the physician or clinician programs the desired pacing rates for LW and HW, and asks the patient to perform the corresponding physical activities for thirty seconds. The last sensor output registered at each level of activity is compared to the desired pacing rate by an algorithm in the programmer and optimal sets of programmable slope and threshold values are suggested to the clinician. The Sensolog 703 pacemaker needs to be manually reprogrammed at various phases after implant, and various tables relating programmable settings to corresponding slope-threshold combinations as well as tables relating rate response to sensor values are also required for programming the parameters.

Medtronic, Inc.'s Legend and Activitrax II models are single-chamber, multi-programmable, rate-responsive pacemakers whose pacing rates vary based upon detected physical activity. These pacemakers have the following programmable parameters: mode, sensitivity, refractory period, pulse amplitude, pulse width, low and upper rate limits, rate response gain, and activity threshold.

Cook Pacemaker Corp.'s Sensor Model Kelvin 500 is a unipolar, multi-modal, rate-responsive, processor-based pacemaker capable of monitoring the temperature of the blood in the heart, and of making the decision to increase the pacing rate as a result of the patient's physiologic stress. This pacemaker allows for the programming of the following parameters: mode, sensitivity, refractory period, pulse width, lower and upper rate limits, and interim rate.

Telectronics' Meta MV Model 1202 is a multi-programmable, bipolar pacemaker. It can be programmed to operate in one of four pacing modes: demand inhibited (VVI or AAI), asynchronous (VOO or AOO), demand inhibited with an automatic rate response based upon sensed changes in respiratory minute ventilation, or adaptive non-rate responsive mode. The following parameters are also programmable for the Model 1202: standby rate, sensitivity, pulse amplitude, pulse width, refractory period, minimum heart rate, and maximum heart rate.

Cordis Pacing Systems' Prism CL Model 450A is a rate-responsive, single-chamber, multi-programmable ventricular pacemaker. The parameters programmable in the Model 450A include: pacing mode, rate-response (on or off), electrode polarity, lower and upper rate limits, output current, output pulse width, sensitivity, refractory period, and automatic calibration speed. In the Prism CL, a dynamic variable called the Rate Control Parameter (RCP) is first determined by an initialization process when rate-response is programmed 'on'. The Prism CL uses the RCP as a reference to control the pacing rate. The pacemaker determines what the appropriate rate should be by comparing the measured RCP to the target RCP. If the measured RCP is different than the target RCP, rate is increased or decreased until the two values are equal. The pacemaker continuously makes automatic adjustments to the target RCP to adjust rate response.

The initial RCP in the Prism CL is determined while the patient is at rest. During initialization, the RCP is measured for approximately twenty paced cycles to establish the target RCP. If intrinsic activity is sensed during the initialization process, initialization is temporarily suspended and the rate is increased by 2.5 pulses per minute (PPM) until pacing resumes. Once initialization is completed and the target RCP has been established, rate response is automatically initiated and the calibration function is enabled. The pacemaker indicates the end of the initialization process by issuing an ECG signature in the succeeding cycle.

The automatic calibration feature of the Prism CL involves continuous calibration of the target RCP and adjustment of the target RCP to compensate for drifts due to lead maturation, drug therapy, and other physiologic factors other than those related to physiologic stresses. The frequency of adjustment depends, in part, on the programmed calibration speed (slow, medium, or fast).

Intermedics, Inc.'s Nova MR is a unipolar (atrial or ventricular) pacemaker which senses variations in blood temperature and uses this information to vary the pacing rate. The following functions are programmable to determined the pacemaker's response to detected variations in blood temperature: rate response, onset detection sensitivity, and post-exercise rate decay.

Vitatron Medical B.V.'s Diamond is a multi-sensor, multi-programmable dual-chamber pacemaker for which a full range of parameters are programmable, including: mode, upper and lower rate limits, maximum tracking and sensor rates, pulse amplitudes and durations, sensitivities, refractory periods, activity acceleration and deceleration, night rate drop, lead polarities, post-stimulation blanking intervals, activity threshold, sensor rate slope, upper rate approach, and numerous others.

The Vitatron Diamond also has a programmably selectable "adaptive AV delay" feature in which the delay between delivery of an atrial stimulating pulse and a ventricular stimulating pulse changes according to the current pacing rate, which itself changes according to detected patient activity. With the adaptive AV delay feature, the physician can select either a fixed AV delay for all pacing rates, or an adaptive AV delay which changes by either six or nine milliseconds for each atrial rate change of ten beats per minute. The adaptive AV delay feature is intended to account for the fact that in a normal, healthy heart, the AV conduction time is inversely proportional to heart rate. See, e.g., Daubert et al., "Physiological Relationship Between AV Interval and Heart Rate in Healthy Subjects: Applications to Dual Chamber Pacing", *PACE*, vol. 9, November–December 1986, Part II, pp. 1032–1039. It has also been shown that rate-adaptive paced AV intervals increase cardiac output. See, e.g., Rees, et al., "Effect of Rate-Adapting Atrioventricular Delay on Stroke Volume and Cardiac Output During Atrial Synchronous Pacing", *Can. Cardiac Journal*, vol. 6., no. 10, December 1990, pp. 445–452. Ideally, a pacemaker's AV delay should be selected to mimic intrinsic AV conduction, since cardiac output is maximized with intrinsic AV conduction. See, e.g., Harper et al., "Intrinsic Conduction Maximizes Cardiopulmonary Performance in Patients With Dual Chamber Pacemakers", *PACE*, vol. 14, November 1991, Part II, pp. 1787–1791. Of course, in patients with high-degree AV block, intrinsic conduction is minimal or non-existent.

Other examples of AV interval rate-adaptation have been shown in the prior art. In U.S. Pat. No. 4,060,090 to Lin et al. entitled "Variable P-R Interval Pacemaker", for example, there is described a circuit for allowing the time between the detection of an atrial contraction and the provision of an electrical stimulus to cause a ventricular contraction to vary with the rate of sensed atrial contractions. In U.S. Pat. No. 4,421,116 to Markowitz entitled "Heart Pacemaker With Separate A—V Intervals for Atrial Synchronous and Atrial-Ventricular Sequential Pacing Modes", there is described a pacemaker having separately definable AV intervals for atrial-synchronous and atrial-ventricular sequential pacing.

The many adjustable parameters for highly sophisticated, fully featured pacemakers, including, for example, the rate-response settings of the Sivula et al. pacemaker and the adaptive AV delay setting of the above-described Vitatron Diamond, have historically been manually programmed and adjusted or optimized to the needs of individual patients on an ad hoc iterative process. Often, because the programming and individualization process is difficult and lengthy, and because the usefulness or effect of certain programmable features may not always be fully appreciated by clinicians, patient parameters are not completely optimized. In some cases, the clinician may simply utilize the nominal default (i.e., shipping) parameter settings. Thus, patients may sometimes not receive the full benefit of a pacemaker's capabilities.

Pacemaker manufacturers have attempted to alleviate the problem of pacemaker optimization by providing extensive diagnostic and monitoring capabilities in their pacemaker systems. For example, the above-described Vitatron Diamond pacemaker offers extensive diagnostic features. The Diamond can transmit event markers to its programmer so that the occurrence of paced and sensed cardiac events can be viewed on a monitor or printed on a strip chart. In addition, the Diamond can generate histograms showing P-wave amplitude, atrial rates, ventricular rate, premature ventricular contraction (PVC) coupling intervals, AV intervals versus atrial rate, VA intervals, atrial rates and PVC, PVC versus time of day, and SVT versus time of day. The Diamond can also function as a 24-hour Holter monitor, or as an activity sensor monitor. Several counters in the Diamond can be interrogated by the programmer to provide the clinician with information such as the percentage of atrial or ventricular paced events, the percentage of sensed evoked T-waves, the percentage of A—V synchronous beats, the number of PVCs, and the period of time during which the atrial rate was above the upper rate limit.

The Vitatron Diamond can also be interrogated by a programming unit to obtain data regarding the lead impedance, actual output voltage, mean output current, T-, P-, and R-wave amplitudes, VA intervals, AV intervals, QT intervals, patient stimulation thresholds, and the like.

With all of this information available, the clinician is theoretically able to make more well-informed choices in parameter selection, thereby better optimizing the operation of the device to the needs of a patient. However, it is important that the information be presented to the clinician in an understandable and meaningful manner, and that the programming process itself not be too difficult or time consuming. Of course, it is also important that the physician or clinician be well-informed about the operation of the pacemaker and about how the various programmable parameters affect its operation.

Even with all of the diagnostic and measurement data available to the clinician, it is sometimes difficult to assimilate all of the information correctly to arrive at optimal pacemaker settings. Often, the interplay between various settings may not be apparent. While it is obvious, for example, that a pacemaker's programmed upper rate must be higher than its programmed lower rate, the interaction between other programmable settings might not be so apparent. For example, in the above-referenced Sivula et al. patent, there is discussed the problem that a selected rate-response slope may not provide for sufficient incrementation to the base pacing rate at maximum sensor output to actually allow the pacemaker to ever reach the programmed upper rate. This defeats the physician's intent in selecting the upper rate, and substantially decreases the physician's ability to fine-tune the pacemaker to the patient's particular needs.

In order to reduce the burden on a clinician in programming a pacemaker, as well as to assist the clinician in making the most appropriate parameter selections, it has been proposed in the prior art that the pacemaker be capable of performing some parameter selection automatically. In co-pending U.S. patent application Ser. No. 07/567,372 filed by Bennett, et al and entitled "Rate Responsive Pacemaker and Method for Automatically Initializing the Same", there is described a pacemaker system capable of automatically initializing such parameters as sensitivity threshold, pacing pulse width, pacing pulse amplitude, activity threshold, and rate-response gain. The Bennett '372 application is hereby incorporated by reference herein in its entirety.

While the teachings of Bennett '372 represents an improvement over prior methods of parameter selection in an implantable pacemaker, the present inventors believe that there is room for further improvements to achieve even greater levels of optimization in pacemaker therapy. In particular, with regard to selectable rate-response settings as well as to the provision of a rate-adaptive AV delay which takes into account the inversely proportional relationship between heart rate and AV intervals, prior implementations (as exemplified by the above-described Vitatron Diamond) have depended on the clinician tailing the rate-response and AV adaptation in a relatively "blind", ad hoc way, usually in the office during a patient follow-up. In addition, the physician is typically limited to selecting from among a relatively few different adaptive AV settings. Moreover, rate-response setting selection and AV interval adjustment are typically done with little diagnostic or hemodynamic performance data to guide the clinician's choices for the patient at hand. Ideally, the tailoring to a patient would be driven by optimization of one or more hemodynamic parameters, such as ejection fraction, ventricular filling, or stroke volume. However, measurement of those parameters requires the presence of special sensors, which may not always be available.

SUMMARY OF THE INVENTION

The present invention, therefore, relates to a method and apparatus for determining a patient's profile for rate-adaptive sense and pace AV intervals and for generally assisting the physician in selecting appropriate available rate-response settings. The disclosed activity exercise test assists the clinician in selecting appropriate rate response parameters and AV rate-adaptation profiles through a defined protocol involving a pacemaker and a programmer. The test results are displayed in novel ways which allow the clinician to observe the impact of activity sensing on the pacing therapy. The clinician can also modify the activity sensor parameters and review the resulting impact. Such forecasting capability allows the clinician to select appropriate sensor parameters based upon information about both the sensor and any intrinsic response that may occur during the exercise. It is believed that the present invention enables a clinician to achieve a greater degree of optimization of a pacemaker's operation to the needs of a given patient.

In accordance with one aspect of the present invention, determination of optimized rate-response and AV rate adaptation is done without extensive and inconvenient hemodynamic measurements, and makes use of the extensive diagnostic capabilities of modern pacemakers.

For patients with high-degree AV block, the clinician could program an AV delay rate-adaptation that mimics the adaptation profile of healthy hearts, and hope that the profile is appropriate for the patient at hand. However, for patients with sufficient intrinsic conduction at certain ranges of heart rate, it may be preferable to allow the intrinsic ventricular contraction to occur so that enhanced ejection fraction, increased myocardial efficiency, and longer pacemaker battery life can be achieved. The present invention relates to a method and apparatus for guiding, and/or automatically making, the selection of rate-adaptive AV parameters for patients with some intrinsic conduction.

In accordance with another aspect of the present invention, an activity testing protocol is conducted on the pacemaker patient, for example at the time of implant or during a patient follow-up. The testing protocol involves a short patient exercise period. The exercise could be a brisk walk or other exercise deemed appropriate for the patient's lifestyle and condition.

During the patient exercise, the pacemaker temporarily sets the programmable AV duration values to be relatively long, (e.g., 250-mSec or so), with zero offset between paced and sensed AV; that is, the AV delay for atrial-sense-to-ventricular-pace (AS-to-VP) is the same as that for atrial-pace-to-ventricular-pace (AP-to-VP). The pacemaker records in its memory every AS-to-VS AV interval duration, if the patient has intrinsic atrial rate at rest, as well as every AP-to-VS AV interval duration. The AV interval duration values are accumulated in "bins" as a function of the atrial rate (counting sensed, paced, and refractory-sensed atrial events to determine atrial rate). The result is a distribution of the two types of AV conduction times in each rate bin.

Also recorded during the exercise test is data reflecting the A—A interval durations, percentage of paced events, and activity sensor detects during the exercise. In addition, the pacemaker records data regarding the percentage of paced events in relation to the total number of cardiac cycles, and this data is similarly accumulated in bins as a function of atrial rate.

At the end of the exercise, the accumulated data is read out of the pacemaker's memory into an external programming/display unit. The data is then displayed by the external unit in ways which show, for the purposes of selecting AV adaptation profiles, the two types of measured AV intervals (i.e., AS-to-VS and AP-to-VS) versus atrial rate, as well as the programmed AV profile, and the "healthy" profile. The programmer interprets the measured pace-sense AV offset, and suggests profiles for the pace and sense AV adaptation. The clinician can accept a suggested profile with one keystroke on the programmer, or else modify the suggested profiles. For the purposes of selecting optimal rate-response settings, the data is displayed in such a way that the physician can observe whether particular rate-response settings are appropriate for the patient.

In accordance with another aspect of the present invention, a pacemaker is provided with the capability to automatically and periodically adjust its AV adaptation profiles, so that the AV rate-adaptive response can be optimized on an ongoing basis. The pacemaker is programmed to assume that if intrinsic conduction is achievable within a maximum allowable rate-dependent AV delay, it is beneficial to allow this. The pacemaker also assumes that the AV delay should decrease linearly with increasing rate. According to a preset schedule, the pacemaker occasionally lengthens the programmed sense and pace AV intervals at a sampling of atrial rates between the programmed upper and lower rates. The pacemaker then fits two linear profiles to these measurements, such that intrinsic conduction will be allowed to occur if it can, and ventricular pacing will occur where intrinsic conduction either doesn't exist or is unacceptably slow.

In accordance with still another feature of the present invention, all of the ambulatory adjustments are recorded in the pacemaker's diagnostic memory for later retrieval and examination by the clinician.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein.

DETAILED DESCRIPTION OF A SPECIFIC EMBODIMENT OF THE INVENTION

Figure 1:
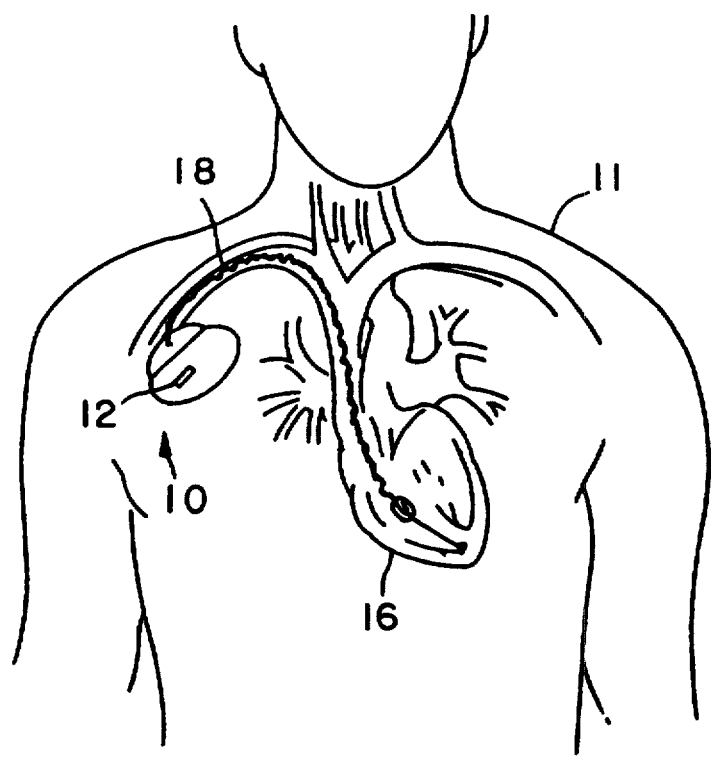
FIG. 1 is an illustration showing the implantation of a pacemaker 10 in accordance with one embodiment of the present invention.
Figure 2:
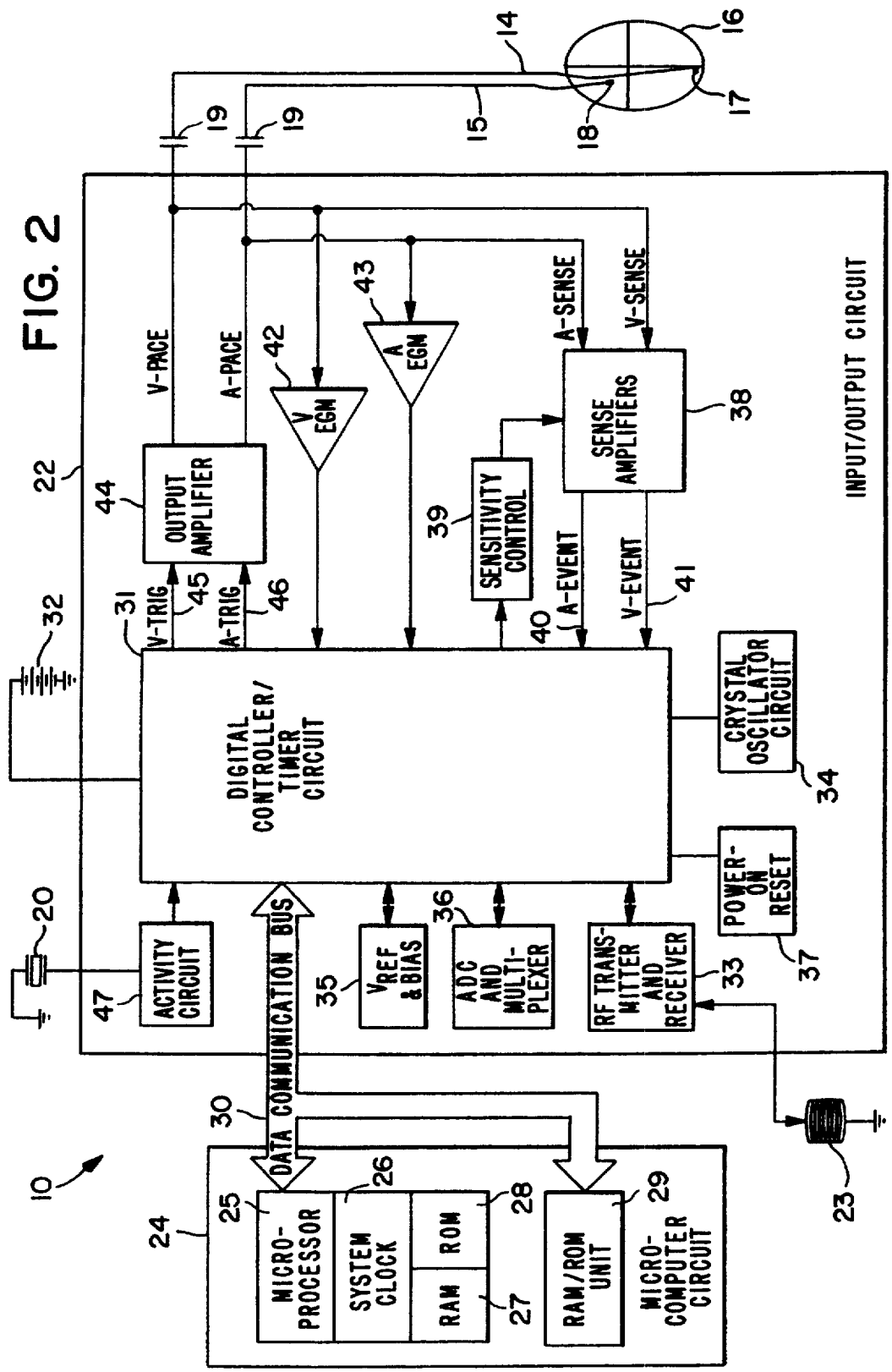
FIG. 2 is a block diagram of the pacemaker of FIG. 1.

FIG. 1 shows generally where a rate-responsive, dual chamber pacemaker 10 in accordance with one embodiment of the present invention may be implanted in a patient 11. It is to be understood that pacemaker 10 is contained within a hermetically-sealed, biologically inert outer shield or "can", in accordance with common practice in the art. One or more conventional pacemaker leads are electrically coupled to pacemaker 10 and extend into the patient's heart 16 via a vein 18. In FIGS. 1 and 2, two such leads, a ventricular lead 14 and an atrial lead 15, are shown. Located on the distal end of leads 14 and 15 are one or more exposed conductive electrodes for receiving electrical cardiac signals and-/or for delivering electrical pacing stimuli to the heart 16. As would be appreciated by those of ordinary skill in the art, dual-chamber pacing can be accomplished with a variety of different lead configurations, including one in which only a single lead having multiple electrodes thereon is used. Thus, although separate atrial and ventricular leads are shown in the Figures, this is done for the purposes of illustration only, and it is to be understood that the present invention is not limited to this particular lead configuration.

In addition, it is contemplated that certain aspects of the present invention may also be advantageously practiced in conjunction with single-chamber, rate-responsive pacemakers.

Turning now to FIG. 2, a block diagram of pacemaker 10 from FIG. 1 is shown. Although the present invention will be described herein in conjunction with a pacemaker 10 having a microprocessor-based architecture, it will be understood that pacemaker 10 may be implemented in any logic based, custom integrated circuit architecture, if desired. The pacemaker shown in FIG. 2 is substantially similar to that disclosed in co-pending U.S. patent application Ser. No. 07/794,766 filed by Stein, et al and entitled "Method and Apparatus for Implementing Activity Sensing in a Pulse Generator", and in co-pending U.S. patent application Ser. No. 07/870,062 filed by Wahlstrand et al. entitled "Method and Apparatus for Rate-Responsive Cardiac Pacing". The Stein '766 and Wahlstrand '062 applications are each hereby incorporated herein by reference in their entireties.

Although a particular implementation of a rate-responsive pacemaker is disclosed herein, it is to be understood that the present invention may be advantageously practiced in conjunction with many different types of rate-responsive pacemakers, such as the pacemaker described in the above-referenced Sivula et al. patent, for example. Furthermore, although the present invention will be described herein in the context of a rate-responsive pacemaker utilizing a microphone-like piezoelectric sensor as described above, it is also to be understood that the present invention may be advantageously practiced in conjunction with pacemakers having other types of sensors (e.g., pressure, blood-oxygen, impedance, temperature, etc . . . ) which provide an indication of a patient's metabolic demand for oxygenated blood.

In the illustrative embodiment shown in FIG. 2, pacemaker 10 includes an activity sensor 20, which may be, for example, a piezoelectric element bonded to the inside of the pacemaker's shield. Such a pacemaker/activity sensor configuration is the subject of the above-referenced patent to Anderson et al. Piezoelectric sensor 20 provides a sensor output which varies as a function of a measured parameter that relates to the metabolic requirements of patient 11.

Pacemaker 10 of FIG. 2 is programmable by means of an external programming unit (not shown in FIG. 2). One such programmer suitable for the purposes of the present invention is the Medtronic Model 9760 programmer which is commercially available and is intended to be used with all Medtronic pacemakers. The 9760 programmer is a microprocessor-based device which provides a series of encoded signals to pacemaker 10 by means of a programming head which transmits radio-frequency (RF) encoded signals to pacemaker 10 according to the telemetry system laid out, for example, in U.S. Pat. No. 5,127,404 to Wyborny et al. entitled "Improved Telemetry Format", which is assigned to the assignee of the present invention and which is incorporated herein by reference in its entirety. It is to be understood, however, that the programming methodology disclosed in the above-referenced patent is identified herein for the purposes of illustration only, and that any programming methodology may be employed so long as the desired information can be conveyed between the pacemaker and the external programmer.

The external programmer should also preferably be capable of displaying both text and graphics, as will be hereinafter become apparent. Also, programmer should be capable of interrogating the pacemaker's internal memory.

It is believed that one of skill in the art would be able to choose from any of a number of available pacemaker programmers and programming techniques to accomplish the tasks necessary for practicing the present invention. As noted above, however, the Medtronic Model 9760 programmer is presently preferred by the inventors. This programmer will be hereinafter described in greater detail with reference to FIG. 3.

In the illustrative embodiment of the present invention, the lower rate of pacemaker 10 may be programmable, for example from 40 to 90 pulses per minute (PPM) in increments of 10 PPM, the upper rate may be programmable between 100 and 175 PPM in 25 PPM increments, and there may be 10 rate response functions, numbered one through ten, available.

In addition, a programmer may include means for selection of acceleration and deceleration parameters which limit the rate of change of the pacing rate. Typically, these parameters are referred to in rate responsive pacemakers as acceleration and deceleration settings, respectively, or attack and decay settings, respectively. These may be expressed in terms of the time interval required for the pacemaker to change between the current pacing rate and 90% of the target pacing interval, assuming that the activity level corresponding to the desired target rate remains constant. Appropriate selectable values for the acceleration time would be, for example, 0.25 minutes, 0.5 minutes, and 1 minute. Appropriate selectable values for the deceleration time would be, for example, 2.5 minutes, 5 minutes, and 10 minutes.

Pacemaker 10 is schematically shown in FIG. 2 to be electrically coupled via pacing lead 14 and 15 to a patient's heart 16. Leads 14 and 15 include one or more intracardiac electrodes, designated as 17 and 18 in FIG. 2, located near their distal ends of leads 14 and 15, respectively, and positioned within the right ventricular (RV) and right atrial (RA) chambers, respectively, of heart 16. As previously noted, leads 14 and 15 can be of either the unipolar or bipolar type as is well known in the art; alternatively, a single, multiple-electrode lead may be used.

Electrodes 17 and 18 are coupled via suitable lead conductors through input capacitors 19 to input/output terminals of an input/output circuit 22. In the presently disclosed embodiment, activity sensor 20 is bonded to the inside of the pacemaker's outer protective shield, in accordance with common practice in the art. As shown in FIG. 2, the output from activity sensor 20 is also coupled to input/output circuit 22.

Input/output circuit 22 contains the analog circuits for interface to the heart 16, activity sensor 20, an antenna 23, as well as circuits for the application of stimulating pulses to heart 16 to control its rate as a function thereof under control of the software-implemented algorithms in a microcomputer circuit 24.

Microcomputer circuit 24 comprises a microprocessor 25 having an internal system clock circuit 26, and on-board RAM 27 and ROM 28. Microcomputer circuit 24 further comprises a RAM/ROM unit 29. Microprocessor 25 and RAM/ROM unit 29 are each coupled by a data and control bus 30 to a digital controller/timer circuit 31 within input/output circuit 22. Microcomputer circuit 24 may be a commercially-available, general-purpose microprocessor or microcontroller, or may be a custom integrated circuit device augmented by standard RAM/ROM components.

It will be understood that each of the electrical components represented in FIG. 2 is powered by an appropriate implantable battery power source 32, in accordance with common practice in the art. For the sake of clarity, the coupling of battery power to the various components of pacemaker 10 has not been shown in the Figures.

An antenna 23 is connected to input/output circuit 22 for purposes of uplink/downlink telemetry through an RF transmitter and receiver unit 33. Unit 33 may correspond to the telemetry and program logic employed in U.S. Pat. No. 4,556,063 issued to Thompson et al. on Dec. 3, 1985 and U.S. Pat. No. 4,257,423 issued to McDonald et al. on Mar. 24, 1981, both of which are incorporated herein by reference in their entirety. Telemetering analog and/or digital data between antenna 23 and an external device, such as the aforementioned external programmer (not shown in FIG. 2), may be accomplished in the presently disclosed embodiment by means of all data first being digitally encoded and then pulse-position modulated on a damped RF carrier, as substantially described in the above-reference patent to Wyborny et al. The particular programming and telemetry scheme chosen is not believed to be important for the purposes of the present invention so long as it provides for entry and storage of values of operational parameters, and for the interrogation of pacemaker memory, as discussed herein.

A crystal oscillator circuit 34, typically a 32,768-Hz crystal-controlled oscillator, provides main timing clock signals to digital controller/timer circuit 31. A $V_{REF}$ and Bias circuit 35 generates stable voltage reference and bias currents for the analog circuits of input/output circuit 22. An analog-to-digital converter (ADC) and multiplexer unit 36 digitizes analog signals and voltages to provide "real-time" telemetry intracardiac signals and battery end-of-life (EOL) replacement function. A power-on-reset (POR) circuit 37 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 30 to digital controller/timer circuit 31 wherein digital timers and counters are employed to establish the overall escape interval of the pacemaker, as well as various refractory, blanking, and other timing windows for controlling the operation of the peripheral components within input/output circuit 22.

Digital controller/timer circuit 31 is coupled to sensing circuitry including a sense amplifier circuit 38 and a sensitivity control circuit 39. In particular, digital controller/timer circuit 31 receives an A-EVENT (atrial event) signal on line 40, and a V-EVENT (ventricular event) signal on line 41. Sense amplifier circuit 38 is coupled to leads 14 and 15, in order to receive the V-SENSE (ventricular sense) and A-SENSE (atrial sense) signals from heart 16. Sense amplifier circuit 38 asserts the A-EVENT signal on line 40 when an atrial event (i.e., a paced or intrinsic atrial event) is detected, and asserts the V-EVENT signal on line 41 when a ventricular event (paced or intrinsic) is detected. Sense amplifier circuit 38 includes one or more sense amplifiers corresponding, for example, to that disclosed in U.S. Pat. No. 4,379,459 issued to Stein on Apr. 12, 1983, incorporated by reference herein in its entirety.

Sensitivity control 39 is provided to adjust the gain of sense amplifier circuitry 38 in accordance with programmed sensitivity settings, as would be appreciated by those of ordinary skill in the pacing art.

A V-EGM (ventricular electrocardiogram) amplifier 42 is coupled to lead 14 to receive the V-SENSE signal from heart 16. Similarly, an A-EGM (atrial electrocardiogram) amplifier 43 is coupled to lead 15 to receive the A-SENSE signal from heart 16. The electrogram signals developed by V-EGM amplifier 42 and A-EGM amplifier 43 are used on those occasions when the implanted device is being interrogated by an external programmer, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference.

Digital controller and timer circuit 31 is coupled to an output amplifier circuit 44 via two lines 45 and 46, designated V-TRIG (ventricular trigger) and A-TRIG (atrial trigger), respectively. Circuit 31 asserts the V-TRIG signal on line 45 in order to initiate the delivery of a ventricular stimulating pulse to heart 16 via pace/- sense lead 14. Likewise, circuit 31 asserts the A-TRIG signal on line 46 to initiate delivery of an atrial stimulating pulse to heart 16 via pace/sense lead 15. Output amplifier circuit 44 provides a ventricular pacing pulse (V-PACE) to the right ventricle of heart 16 in response to the V-TRIG signal developed by digital controller/timer circuit 31 each time the ventricular escape interval times out, or an externally transmitted pacing command has been received, or in response to other stored commands as is well known in the pacing art. Similarly, output amplifier circuit 44 provides an atrial pacing pulse (A-PACE) to the right atrium of heart 16 in response to the A-TRIG signal developed by digital controller/timer circuit 31. Output amplifier circuit 44 includes one or more output amplifiers which may correspond generally to the that disclosed in U.S. Pat. No. 4,476,868 issued to Thompson on Oct. 16, 1984 also incorporated herein by reference in its entirety.

As would be appreciated by those of ordinary skill in the art, input/output circuitry will include decoupling circuitry for temporarily decoupling sense amplifier circuit 38, V-EGM amplifier 42 and A-EGM amplifier 43 from leads 14 and 15 when stimulating pulses are being delivered by output amplifier circuit 44. For the sake of clarity, such decoupling circuitry is not depicted in FIG. 2.

While specific embodiments of sense amplifier circuitry, output amplifier circuitry, and EGM amplifier circuitry have been identified herein, this is done for the purposes of illustration only. It is believed by the inventor that the specific embodiments of such circuits are not critical to the present invention so long as they provide means for generating a stimulating pulse and provide digital controller/timer circuit 31 with signals indicative of natural and/or stimulated contractions of the heart. It is also believed that those of ordinary skill in the art could chose from among the various well-known implementations of such circuits in practicing the present invention.

Digital controller/timer circuit 31 is coupled to an activity circuit 47 for receiving, processing, and amplifying activity signals received from activity sensor 20. A suitable implementation of activity circuit 47 is described in detail in the above-referenced Sivula et al. '388 patent. It is believed that the particular implementation of activity circuit 47 is not critical to an understanding of the present invention, and that various activity circuits are well-known to those of ordinary skill in the pacing art.

Figure 3:
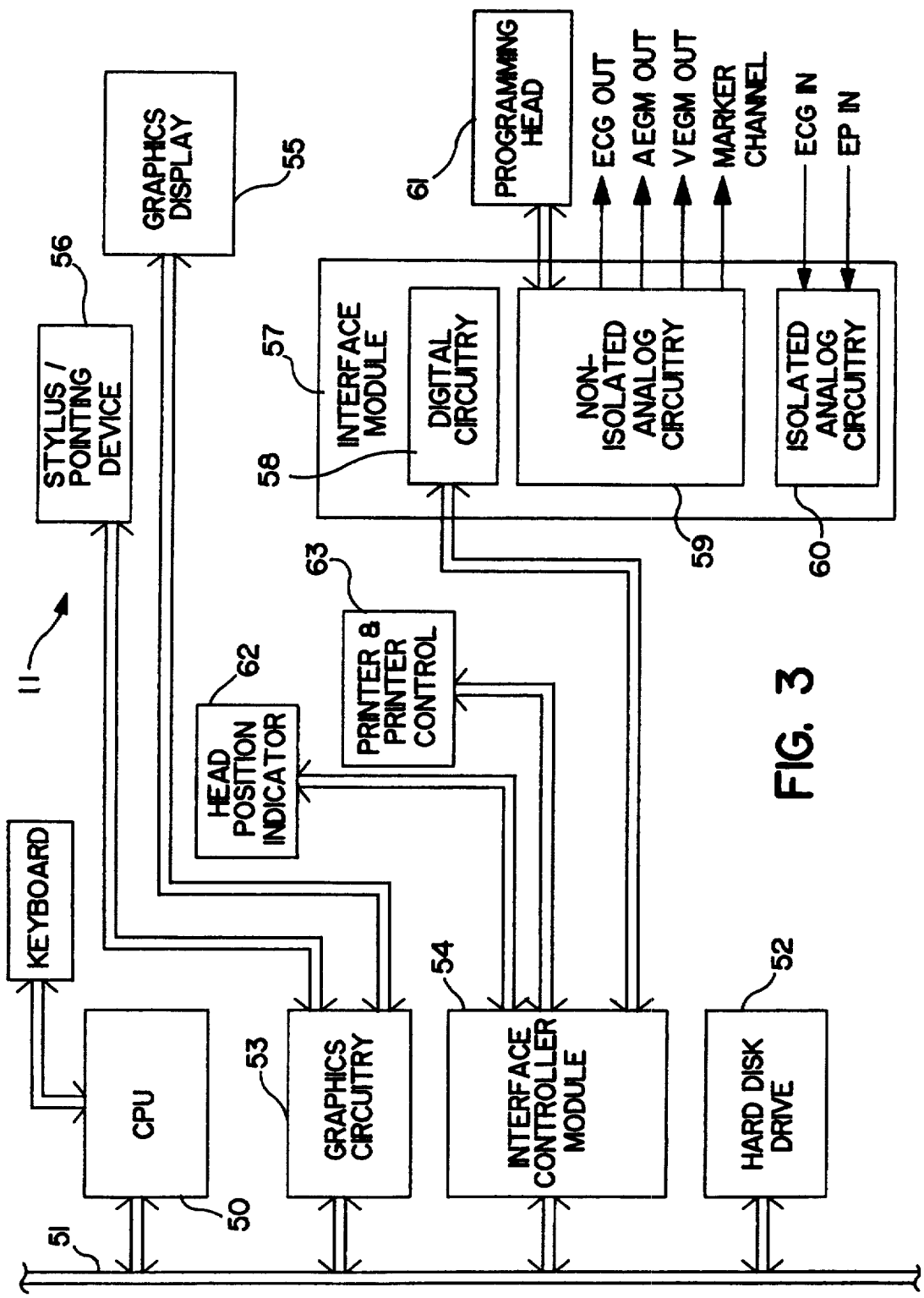
FIG. 3 is a block diagram of an external programming unit in accordance with the disclosed embodiment of the invention.

A generalized block diagram of programmer 11 in accordance with the presently disclosed embodiment of the invention is provided in FIG. 3. As shown in FIG. 3, programmer 11 is a personal-computer type microprocessor-based device incorporating, a central processing unit 50, which may be, for example, an Intel 80386 microprocessor or the like.

A system bus 51 interconnects CPU 50 and various other components of programmer 11. For example, bus 51 provides a connection between CPU 50 and a hard disk drive 52 storing operational programming for programmer 11. Also coupled to system bus 51 is a graphics circuit 53 and an interface controller module 54.

Graphics circuit 53, in turn, is coupled to a graphics display screen 55, which in the case of the Medtronic Model 9760 programmer is a cathode ray tube (CRT) screen 55 having a resolution of 720×348 pixels. In the presently preferred embodiment of the invention, screen 55 is of the well-known "touch sensitive" type, such that a user of programmer 11 may interact therewith through the use of a stylus 56, also coupled to graphics circuit 53, which is used to point to various locations on screen 55. Various touch-screen assemblies are known and commercially available.

With continued reference to FIG. 3, programmer 11 further comprises an interface module 57 which includes digital circuitry 58, non-isolated analog circuitry 59, and isolated analog circuitry 60. Digital circuitry 58 enables interface module 57 to communicate with interface controller module 54.

Non-isolated analog circuitry 59 in interface module 57 has coupled thereto a programming head 61 which, as would be appreciated by those of ordinary skill in the art, is used to establish a telemetry link between an implanted device and programmer 11. In particular, programming head 61 is placed over the implant site of pacemaker 10 in a patient, and includes a telemetry coil for transmitting and receiving RF signals.

As previously noted, pacemaker 10 is provided with EGM amplifiers 42 and 43 which produce ventricular and atrial EGM signals. These EGM signals may be digitized by ADC 36 and up-link telemetered to programmer 11. The telemetered EGM signals are received in programming head 61 and provided to non-isolated analog circuitry 59. Non-isolated analog circuitry 59, in turn, converts the digitized EGM signals to analog EGM signals (as with a digital-to-analog converter, for example) and presents these signals on output lines designated in FIG. 3 as A EGM OUT and V EGM OUT. These output lines may then be applied to a strip-chart recorder, CRT, or the like, for viewing by the physician. As these signals are ultimately derived from the intracardiac electrodes, they often provide different information that may not be available in conventional surface ECG signals derived from skin electrodes.

Pacemaker 10 may also be capable of generating so-called marker codes indicative of different cardiac events that it detects. A pacemaker with marker-channel capability is described, for example, in U.S. Pat. No. 4,374,382 to Markowitz entitled "Marker Channel Telemetry System for a Medical Device", which patent is hereby incorporated by reference herein in its entirety. The markers provided by pacemaker 10 may be received by programming head 61 and presented on the MARKER CHANNEL output line from non-isolated analog circuitry 59.

Isolated analog circuitry 60 in interface module 57 is provided to receive ECG and EP signals. In particular, analog circuitry 60 receives ECG signals from patient skin electrodes and processes these signals before providing them to the remainder of the programmer system. Circuitry 60 further operates to receive electrophysiologic (EP) stimulation pulses from an external EP stimulator, for the purposes of non-invasive EP studies, as would be appreciated by those of ordinary skill in the art.

In order to ensure proper positioning of programming head 61 over implanted device 10, circuitry is commonly provided for providing feedback to the user that programming head 61 is in satisfactory communication with and is receiving sufficiently strong RF signals from pacemaker 10. This feedback may be provided, for example, by means of a head position indicator, designated as 61 in FIG. 3. Head position indicator 62 may be, for example, a light-emitting diode (LED) or the like that is lighted to indicate a stable telemetry channel.

Programmer 11 is also provided with a strip-chart printer or the like, designated in 63 in FIG. 3, which may be used, for example, to provide a hard-copy printout of the A EGM or V EGM signals transmitted from pacemaker 10.

In the presently disclosed embodiment of the invention, there are a number of counters, registers, and timers implemented in the digital controller/timer circuit 31 of pacemaker 10. These registers and counters are used for measuring certain time intervals necessary for carrying out the pacing/rate-response algorithm and other functions of pacemaker 10. The use of counters, registers, and timers for this purposes is well-known in the art, and is also described in the above-referenced co-pending applications to Stein and to Wahlstrand et al. One counter in circuit 31 is called the PACE COUNTER, and is used to store a numeric value corresponding to the number of pacing stimuli delivered by the device. As would be appreciated by those of ordinary skill in the art, for dual-chamber pacemakers, two count values could be maintained, an APACE COUNTER reflecting the number of atrial stimulating pulses delivered and a VPACE COUNTER reflecting the number of ventricular stimulating pulses delivered. Another counter is called the TOTAL EVENT COUNTER, and is used to store a numeric value corresponding to the number of cardiac events which occur. Still another counter relevant to the presently disclosed embodiment of the invention is an ACTIVITY COUNTER, which is used to count the number of sensor detects. Therefore, if it is desired, for example, to count the number of ventricular pacing pulses delivered during a given interval, circuit 31 will reset the VPACE COUNTER at the beginning of the interval of interest, and then cause the value of the VPACE COUNTER to be incremented by one each time the V-TRIG signal is asserted. Similarly, if it is desired to count the number of cardiac cycles (e.g., A—A intervals) occurring during a given time interval, circuit 31 will reset the TOTAL EVENT COUNTER at the beginning of the interval of interest, and then cause the value of the TOTAL EVENT COUNTER to be incremented by one each time the A-EVENT signal is asserted by sense amplifier circuitry 38, and each time ATRIG is asserted by digital circuit 31. (Of course, the number of cardiac cycles could also be determined by counting the number of V—V intervals, in which case the TOTAL EVENT COUNTER would be incremented by one each time the V-EVENT signal is asserted.)

One of the timers implemented in circuit 31 is called the INTERVAL TIMER and is used to measure the duration of cardiac cycles (i.e., A—A intervals or V—V intervals). Another timer, called the AV TIMER, is used to measure the duration of A—V intervals (i.e., the interval between an atrial paced or sensed event and a ventricular paced or sensed event). As would be appreciated by those of ordinary skill in the art, the INTERVAL TIMER, AV TIMER, and other timers to be described in greater detail below, are, in actuality, counters which receive a clock signal at an increment or decrement input thereto, such that the counter value is incremented or decremented by one each clock cycle. The real-time duration of an interval measured by such counters can then be determined based upon the counter value at the end of the interval in question and the frequency of the clock signal applied to the counter. In the presently disclosed embodiment of the invention, it will be assumed that the timers in circuit 31 are clocked by a 128-Hz clock signal, which of course can be readily derived from the system clock signal from crystal oscillator circuit 34.

As pacemaker 10 may be a dual-chamber pacemaker having both atrial and ventricular sensing capabilities, a cardiac cycle may be defined in terms of either and A—A interval (i.e., the interval from one atrial event, paced or sensed, to the next), or a V—V interval (i.e., the interval from one ventricular event, paced or sensed, to the next). Naturally, if pacemaker 10 were a single-chamber pacemaker having sensing capabilities in only one chamber, a cardiac cycle would of necessity be defined in terms of successive events in the sensed chamber. For the purposes of the following description, the term "cardiac cycle" will be used to indicate an A—A interval, although it is to be understood that a cardiac cycle could also be defined in terms of V—V intervals.

In accordance with the presently disclosed embodiment of the invention, pacemaker 10 performs a number of operations at the end of each cardiac cycle. At the end of each cardiac cycle, circuit 31 will cause the value held in the INTERVAL TIMER to be stored in memory 29. Microcomputer circuit 24 maintains an area of successive memory locations in RAM/ROM unit 29 for storing successive INTERVAL TIMER values, so that information regarding the length of a plurality of recent cardiac cycles can be subsequently retrieved. The INTERVAL TIMER is reset following each cardiac cycle, so that the value of the INTERVAL TIMER at the end of a cardiac cycle reflects the duration of that cardiac cycle. Also, at the end of each cardiac cycle, circuit 31 increments the value of the PACE COUNTER by one if an atrial stimulating pulse was delivered during the cycle. (Again, it is to be understood that cardiac cycles could also be defined in terms of V—V intervals, in which case the PACE COUNTER would be incremented if a ventricular stimulating pulse was delivered during the cycle. It is also contemplated that separate counters and timers could be maintained for both the atrium and the ventricle; however, the consumption of memory and processing capability may mandate that only one chamber or the other could be monitored.)

For the purposes of implementing the rate-response algorithm described in the above-referenced U.S. patent applications to Stein and to Wahstrand et al., pacemaker 10 also performs a number of operations at the end of each two-second interval.

As noted above, the present invention involves, in one aspect, the performance of a brief (e.g., five minute) exercise, during which time data regarding heart and pacemaker function is collected by pacemaker 10. In particular, during the activity test, pacemaker 10 performs certain operations and stores data at the end of each cardiac cycle. In a similar manner, pacemaker 10 performs some additional operations and stores data at the end of each two-second time interval during the activity test. The activity test assists the clinician in selecting appropriate rate-response parameter settings and AV adaptation settings through defined protocols.

After the activity test, the exercise data is conveyed to and graphically displayed on display screen 55 of programmer 11. The clinician is thereby enabled to graphically see the effects of changing rate-response parameters.

Generally speaking, two sets of data are gathered by pacemaker 10 during the activity test. One set consists of data collected at the end of each cardiac cycle during the test, and another set consists of data collected at the end of each two-second interval during the test.

In particular, at the end of each cardiac cycle, the INTERVAL TIMER duration of that cardiac cycle is converted into a "bin number" according to an algorithm to be hereinafter described in greater detail. This bin number reflects a range of heart rates, such that higher bin numbers correspond to higher heart rates. Then, data corresponding to the duration of the AV interval for the latest cardiac cycle is stored along with the bin number for that cycle. Along with the AV interval and bin data, some identification is made as to whether the AV data reflects an atrial sense-to-ventricular sense (AS-to-VS) or atrial pace-to-ventricular sense (AP-to-VS) interval. It is contemplated that a single bit of data (i.e., a one or a zero) could be used to distinguish AS-to-VS AV data from AP-to-VS data.

At the end of each two second interval, the INTERVAL TIMER value reflecting the duration of the last cardiac cycle in the two-second interval is converted into a bin number using the bin-calculation algorithm. Also, microcomputer circuit 24 computes the percentage of paced events (PERCENT PACED) during the two-second interval, and determines the number of sensor detects during the two-second interval. The sensor detects value, percent paced value, and bin number associated with each two-second interval are then packed together into two bytes and stored in memory 29 at the end of that interval.

It is contemplated that a four-second interval, rather than a two-second interval, could be used in the practice of the present invention. This increase would halve the amount of data generated, thereby reducing memory capacity constraints. However, this would constitute a decrease in the "resolution" of the resulting computations or double the duration of recording capability.

Figure 4:
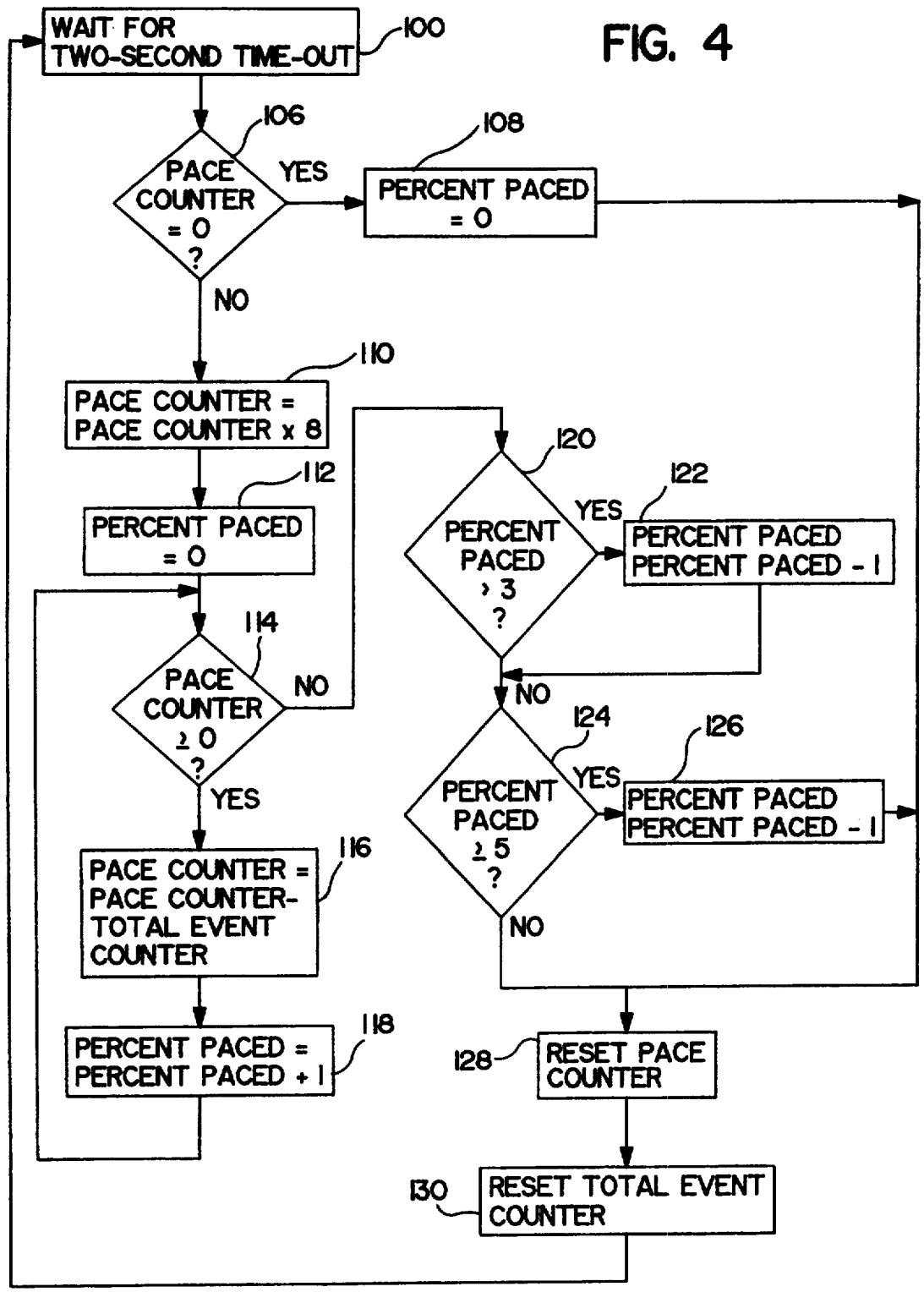
FIG. 4 is a flow diagram illustrating the algorithm for determining the percentage of paced events during the exercise test in accordance with the disclosed embodiment of the invention.

Turning now to FIG. 4, there is shown a flow chart depicting the steps involved in the computation of the PERCENT PACED value at the end of each two-second interval of the exercise test. Block 100 in FIG. 4 indicates that the bin computation is performed only at the end of each two-second interval, as previously described. At the end of the two-second interval, microcomputer 24 determines whether the PACE COUNTER value is equal zero, (i.e., no paced events during the last two-second interval), as indicated by decision block 106 in FIG. 4. If so, PERCENT PACED is assigned a value of zero, in block 108. If some paced events did occur during the two-second interval, flow proceeds to block 110, where the PACE COUNTER value is multiplied by eight, and then to block 112, where the PERCENT PACED value is initialized to zero. Next, in block 114, it is determined whether the PACE COUNTER value is greater than or equal to zero. If the PACE COUNTER value is greater than or equal to zero, the current PACE COUNTER value is assigned a value corresponding to the PACE COUNTER value minus the TOTAL EVENT COUNTER value, in block 116, and the PERCENT PACED VALUE is incremented by one, in block 118.

From block 118, flow returns to decision block 114, where it is again determined whether the current PACE COUNTER value is greater than zero. The PACE COUNTER value may not be greater than zero, since it has just been reassigned a value in block 116.

When the PACE COUNTER value becomes less than zero in block 114, flow proceeds to decision block 120, where a determination is made whether the PERCENT PACED value is greater than three. If so, PERCENT PACED is decremented by one, in block 122, and then flow proceeds to block 124. If the PERCENT PACED value was less than or equal to three in block 120, a determination is made in block 124 whether the PERCENT PACED value is greater than or equal to five. If so, PERCENT PACED is decremented by one, in block 126. However, if the PERCENT PACED value was less than five in block 124, flow proceeds to block 128. Flow also proceeds to block 128 from block 126. The PACE COUNTER value is reset to zero in block 128, and then the TOTAL EVENT COUNTER is reset in block 130. Then, the PERCENT PACED algorithm terminates, until the end of the next two-second interval. The algorithm just described with reference to FIG. 4 may alternatively be expressed in the form of a pseudo-code subroutine, as follows:

```
IF (PACE COUNTER = 0) THEN
    PERCENT PACED = 0
ELSE
    PACE COUNTER = PACE COUNTER × 8
    PERCENT PACED = 0
    WHILE (PACE COUNTER ≥ 0)
        PACE COUNTER = PACE COUNTER −
            TOTAL EVENT COUNTER
        PERCENT PACED = PERCENT PACED + 1
    IF (PERCENT PACED > 3) THEN
        PERCENT PACED = PERCENT PACED − 1
    IF (PERCENT PACED ≥ 5) THEN
        PERCNET PACED = PERCENT PACED − 1
    PACE COUNTER = 0
    TOTAL EVENT COUNTER = 0
```

The PERCENT PACED value obtained from the foregoing algorithm (hereinafter "the percent paced algorithm") will be in the range between zero and seven, inclusive. The PERCENT PACED value correlates to a displayed percentage range (DPR) according to the following Table 1:

TABLE 1

| PERCENT PACED | DISPLAYED PERCENTAGE RANGE (DPR) |
|---|---|
| 0 | DPR = 0 |
| 1 | 0 < DPR < 12.5 |
| 2 | 12.5 ≤ DPR < 25 |
| 3 | 25 ≤ DPR < 50 |
| 4 | 50 ≤ DPR < 75 |
| 5 | 75 ≤ DPR < 87.5 |
| 6 | 87.5 ≤ DPR < 100 |
| 7 | DPR = 100 |

After a PERCENT PACED value has been obtained for the latest two-second interval, it is stored in three bits of the current RAM location (i.e., the location in RAM unit 29 corresponding to the latest two-second interval).

Figure 5:
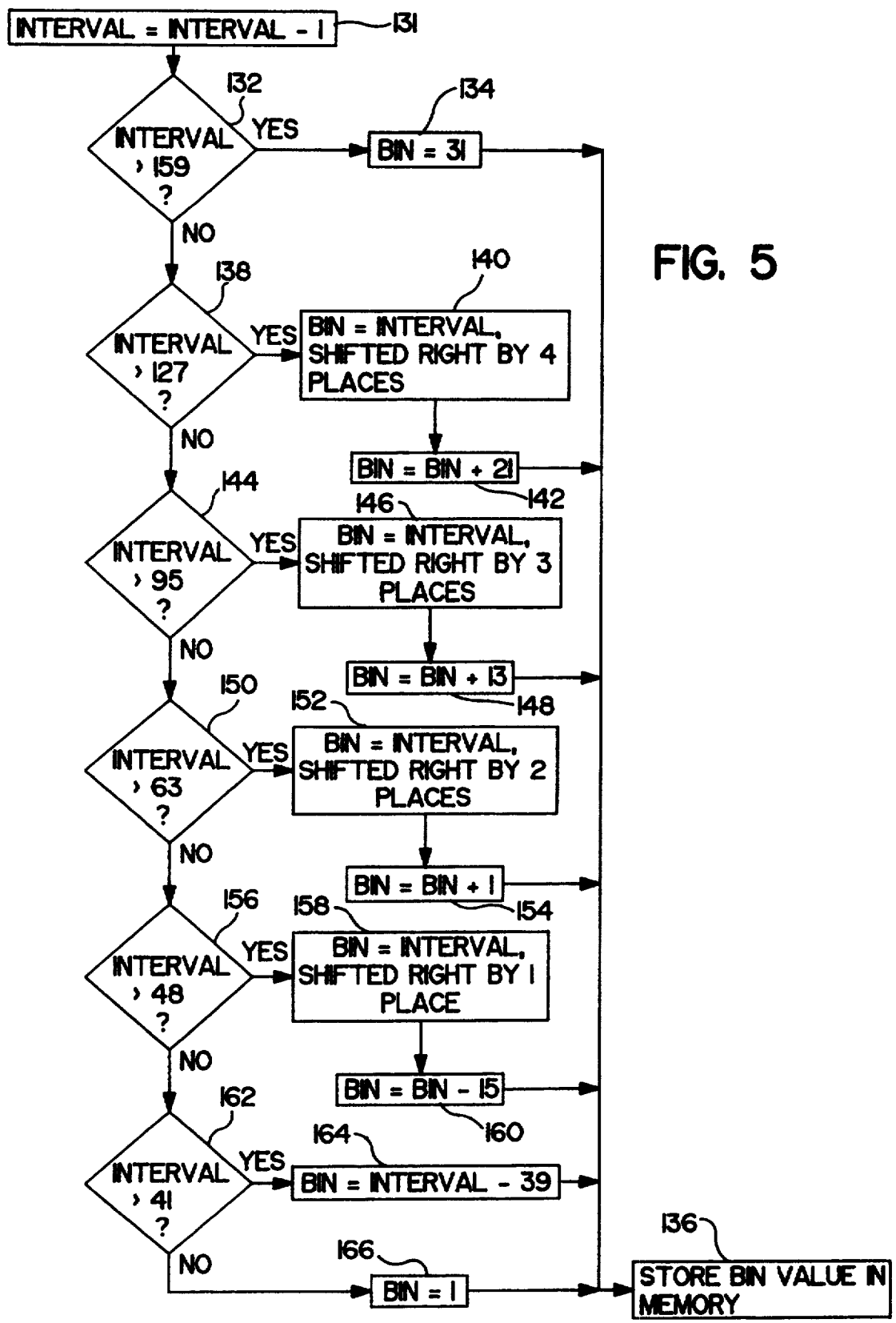
FIG. 5 is a flow diagram illustrating the algorithm for computing a bin value as a function of atrial rate in accordance with the disclosed embodiment of the invention.

In FIG. 5, there is shown a flow diagram illustrating the algorithm performed by pacemaker 10 for converting an INTERVAL TIMER value into a bin number corresponding to a range of heart rates. It is to be understood that the computations described with reference to FIG. 5 are based on an assumed clock rate of 128-Hz, and that the INTERVAL TIMER maintained in digital controller/timer circuit 31 is decremented by one on each clock cycle, starting with an initial value of 256. Of course, if a different clock rate were used, certain numeric values in the bin calculation algorithm would have to be changed.

As previously noted, the bin-computation algorithm depicted in FIG. 5 is performed by pacemaker 10 at the end of each cardiac cycle, based upon the A—A interval of that cycle, and at the end of each two-second interval. In the case of the computations performed at the end of each two-second interval, the bin computation is based upon the duration of the last cardiac cycle in that interval.

The algorithm depicted in FIG. 5 begins at block 131, where the current INTERVAL TIMER value is decremented by one. Next, flow proceeds to decision block 132, where a determination is made (by microcomputer circuit 24) whether the INTERVAL TIMER value for the last cardiac cycle in the latest two-second interval is greater than 159 (recall that the INTERVAL TIMER value reflects the number of cycles of the 128-Hz clock in the cardiac cycle). If the INTERVAL TIMER value is greater than 159, the BIN value is set to 31 in block 134, and this BIN value is stored (as indicated by block 136 in FIG. 5) in the remaining five bits of the byte containing the three-bit PERCENT PACED value previously described with reference to FIG. 4.

On the other hand, if the INTERVAL TIMER value is less than or equal to 159, flow proceeds from block 132 to decision block 138, where a determination of whether the INTERVAL TIMER value is greater than 127. If the INTERVAL TIMER value is greater than 127, BIN is assigned an initial value corresponding to the INTERVAL TIMER value shifted right by four binary places (i.e., the INTERVAL TIMER value divided by sixteen), in block 140. Then 21 is added to this initial BIN value, in block 142, to obtain a final BIN value, which is stored in memory (block 136).

If the INTERVAL TIMER value was less than or equal to 127 in block 138, flow proceeds to decision block 144. From block 144, if the INTERVAL TIMER value is found to be greater than 95, BIN is assigned an initial value, in block 146, corresponding to the INTERVAL TIMER value shifted right by 3 binary places (i.e., the INTERVAL TIMER value divided by eight). Then, 13 is added to this initial BIN value, in block 148, to obtain a final BIN value which is stored in memory (block 136).

If the INTERVAL TIMER value was found to be less than or equal to 95 in block 144, flow proceeds to decision block 150. From block 150, if the INTERVAL TIMER value is found to be greater than 63, BIN is assigned an initial value, in block 152, corresponding to the INTERVAL TIMER value shifted right by 2 binary places (i.e., the INTERVAL TIMER value divided by four). Then, this initial BIN value is incremented by one, in block 154, to obtain a final BIN value which is stored in memory (block 136).

If the INTERVAL TIMER value was found to be less than or equal to 63 in block 150, flow proceeds to decision block 156. From block 156, if the INTERVAL TIMER value is found to be greater than 48, BIN is assigned an initial value, in block 158, corresponding to the INTERVAL TIMER value shifted right by one binary places (i.e., the INTERVAL TIMER value divided by two). Then, fifteen is subtracted from this initial BIN value, in block 160, to obtain a final BIN value which is stored in memory (block 136).

If the INTERVAL TIMER value was found to be less than or equal to 49 in block 156, flow proceeds to decision block 162. From block 162, if the INTERVAL TIMER value is found to be greater than 41, BIN is assigned a value, in block 164, corresponding to the INTERVAL TIMER value minus 39. This BIN value is then stored in memory (block 136).

Finally, if the INTERVAL TIMER value was found to be less than or equal to 40 in block 162, BIN is assigned a value of one, and this value is stored in memory (block 136).

The bin-computation algorithm just described with reference to FIG. 5 can alternatively be expressed in the form of a pseudo-code subroutine, as follows:

```
INTERVAL TIMER = INTERVAL TIMER − 1
IF (INTERVAL TIMER VALUE > 159) THEN
   BIN = 31
ELSE IF (INTERVAL TIMER VALUE > 127) THEN
   BIN = INTERVAL TIMER VALUE SHIFTED RIGHT
   4 PLACES
   BIN = BIN + 21
ELSE IF (INTERVAL TIMER VALUE > 95) THEN
   BIN = INTERVAL TIMER VALUE SHIFTED RIGHT
   3 PLACES
   BIN = BIN + 13
ELSE IF (INTERVAL TIMER VALUE > 63) THEN
   BIN = INTERVAL TIMER VALUE SHIFTED RIGHT
   2 PLACES
   BIN = BIN + 1
ELSE IF (INTERVAL TIMER VALUE > 48) THEN
   BIN = INTERVAL TIMER VALUE SHIFTED RIGHT
   1 PLACE
   BIN = BIN − 15
ELSE IF (INTERVAL TIMER VALUE > 41) THEN
   BIN = INTERVAL TIMER VALUE − 39
ELSE BIN = 1
```

In the following Table 2, there is set forth the correspondence between the BIN values calculated according to the algorithm depicted in FIG. 5, the displayed rate range (DR) for each BIN, the range of INTERVAL TIMER values (It) corresponding to each BIN, and the range of real-time heart rates (HR) corresponding to each BIN. Again, it is to be understood that the INTERVAL TIMER values are based on a 128-HZ clock.

TABLE 2

| COMPUTED BIN VALUE | DISPLAYED RATE RANGE (DR) (beats per minute) | INTERVAL TIMER RANGE (IT) | HEART RATE RANGE (HR) (beats per minute) |
|---|---|---|---|
| 31 | 0 < DR < 50 | $161 \leq IT \leq 255$ | $30.00 \leq HR \leq 47.70$ |
| 30 | 51 < DR < 55 | $145 \leq IT \leq 160$ | $48.00 \leq HR \leq 52.97$ |
| 29 | 56 < DR < 60 | $129 \leq IT \leq 144$ | $53.33 \leq HR \leq 59.53$ |
| 28 | 61 < DR < 65 | $121 \leq IT \leq 128$ | $60.00 \leq HR \leq 63.47$ |
| 27 | 66 < DR < 70 | $113 \leq IT \leq 120$ | $64.00 \leq HR \leq 67.96$ |
| 26 | 71 < DR < 75 | $105 \leq IT \leq 112$ | $68.57 \leq HR \leq 73.14$ |
| 25 | 76 < DR < 80 | $97 \leq IT \leq 104$ | $73.84 \leq HR \leq 79.17$ |
| 24 | 81 < DR < 85 | $93 \leq IT \leq 96$ | $80.00 \leq HR \leq 82.58$ |
| 23 | 86 < DR < 90 | $89 \leq IT \leq 92$ | $83.48 \leq HR \leq 86.29$ |

TABLE 2-continued

| COMPUTED BIN VALUE | DISPLAYED RATE RANGE (DR) (beats per minute) | INTERVAL TIMER RANGE (IT) | HEART RATE RANGE (HR) (beats per minute) |
|---|---|---|---|
| 22 | $91 < DR < 95$ | $85 \leq IT \leq 88$ | $87.27 \leq HR \leq 90.35$ |
| 21 | $96 < DR < 100$ | $81 \leq IT \leq 84$ | $91.43 \leq HR \leq 94.81$ |
| 20 | $101 < DR < 105$ | $77 \leq IT \leq 80$ | $96.00 \leq HR \leq 99.74$ |
| 19 | $106 < DR < 110$ | $73 \leq IT \leq 76$ | $101.05 \leq HR \leq 105.21$ |
| 18 | $111 < DR < 115$ | $69 \leq IT \leq 72$ | $106.67 \leq HR \leq 111.30$ |
| 17 | $116 < DR < 120$ | $65 \leq IT \leq 68$ | $112.94 \leq HR \leq 118.15$ |
| 16 | $121 < DR < 125$ | $63 \leq IT \leq 64$ | $120.00 \leq HR \leq 121.90$ |
| 15 | $126 < DR < 130$ | $61 \leq IT \leq 62$ | $123.87 \leq HR \leq 125.90$ |
| 14 | $131 < DR < 135$ | $59 \leq IT \leq 60$ | $128.00 \leq HR \leq 130.17$ |
| 13 | $136 < DR < 140$ | $57 \leq IT \leq 58$ | $132.41 \leq HR \leq 134.74$ |
| 12 | $141 < DR < 145$ | $55 \leq IT \leq 56$ | $137.14 \leq HR \leq 139.64$ |
| 11 | $146 < DR < 150$ | $53 \leq IT \leq 54$ | $142.22 \leq HR \leq 144.91$ |
| 10 | $151 < DR < 155$ | $51 \leq IT \leq 52$ | $147.69 \leq HR \leq 150.59$ |
| 9 | $156 < DR < 160$ | $49 \leq IT \leq 50$ | $153.60 \leq HR \leq 156.73$ |
| 8 | $161 < DR < 165$ | $IT = 48$ | $HR = 160.00$ |
| 7 | $DR = 166$ | $IT = 47$ | $HR = 163.40$ |
| 6 | $DR = 170$ | $IT = 46$ | $HR = 166.96$ |
| 5 | $171 < DR < 175$ | $IT = 45$ | $HR = 170.67$ |
| 4 | $DR = 176$ | $IT = 44$ | $HR = 174.54$ |
| 3 | $DR = 180$ | $IT = 43$ | $HR = 178.60$ |
| 2 | $181 < DR < 185$ | $IT = 42$ | $HR = 182.86$ |
| 1 | $186 < DR < 190$ | $0 \leq IT \leq 41$ | $187.32 \leq HR \leq URL$ |

As noted above, the activity test in accordance with the presently disclosed embodiment of the invention involves a brief period of patient exercise, preferably on the order of five minutes or so, during which time pacemaker 10 stores data in RAM 29 after each cardiac cycle (A—A interval) and after each two-second interval. The first byte stored after each two-second interval contains the BIN and PERCENT PACED values obtained as just described, while the second byte contains the sensor detects count for the two-second interval. These bytes are stored as successive two-byte pairs in a reserved portion of RAM 29, so that they may be subsequently retrieved through interrogation by programmer 11 in the order of storage.

It is contemplated that a special case may be defined wherein the two bytes stored following a two second interval are both zero bytes. This special case could be used to indicate that a reed switch closure occurred while the exercise test was in progress.

It should be noted that the rate-response algorithm described in the above-referenced co-pending Stein and Wahlstrand et al. applications use the same two-second sensor detects data that is stored during the activity test in accordance with the presently disclosed embodiment of the invention. Thus, when the sensor detects data accumulated during the exercise test is provided to external programmer 11, programmer 11 is able to independently execute the same rate-response algorithm that is performed internally by pacemaker 10, using the same rate-response parameter settings that are programmed into pacemaker 10. In addition, however, programmer 11 can perform the rate-response computations on the data using different rate-response parameter settings, so that the clinician may determine what the pacemaker's rate-response would have been with the different settings, given the same activity levels of the patient during the activity test. This allows the clinician to experiment with different rate-response settings to determine if a different combination of rate-response settings might have resulted in better rate-response in pacemaker 10 to the patient's activity.

Figure 6:
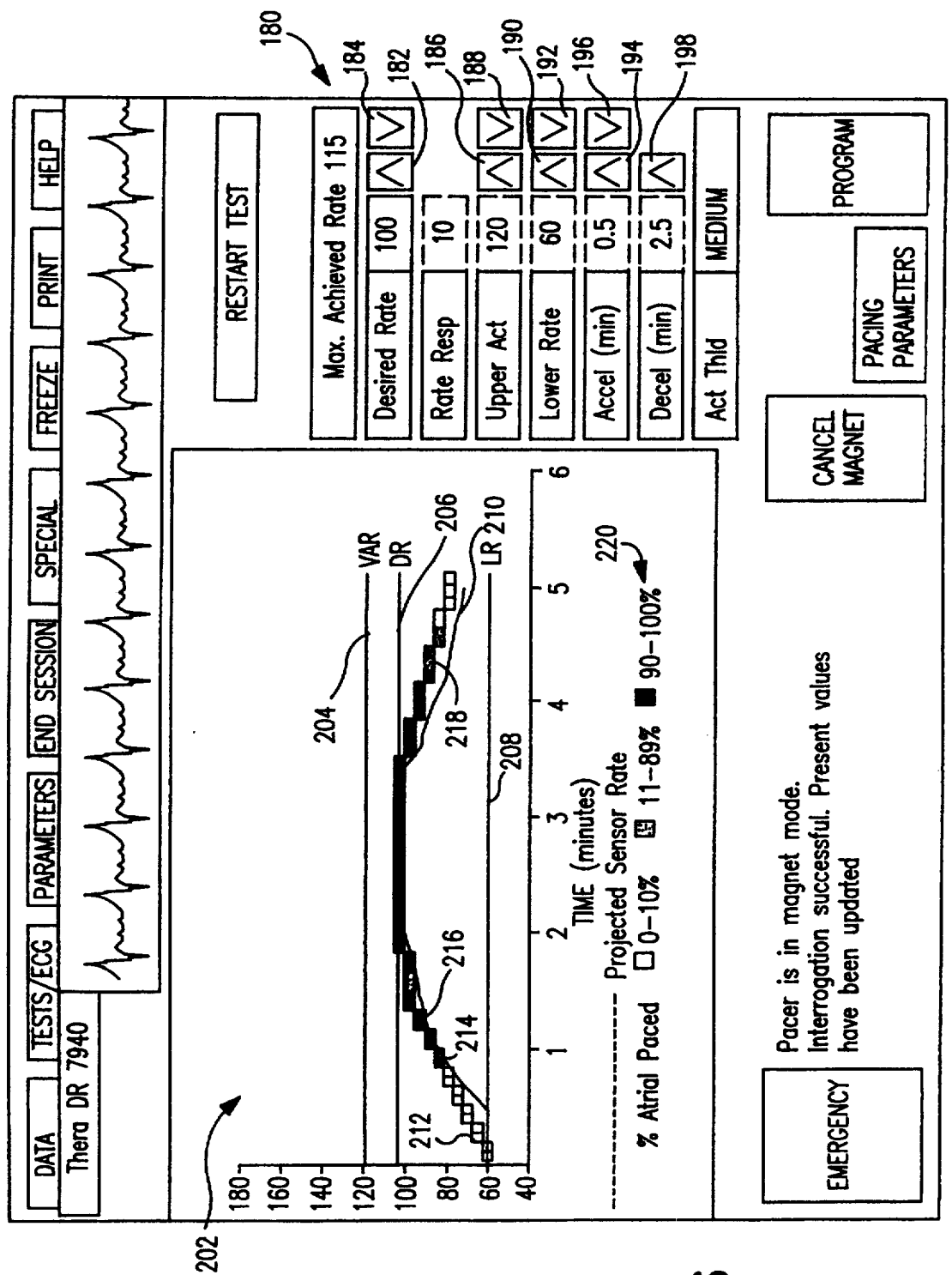
FIG. 6 is an illustration of a programmer display screen in accordance with the disclosed embodiment of the invention.

Turning now to FIG. 6, there is shown a reproduction of a display of the activity-test data by programmer 11. As previously noted, it is believed that the details of implementation of a pacemaker programmer capable of displaying graphics such as shown in FIG. 6 are not essential to an understanding of the present invention, and that those of ordinary skill in the art would be readily able to select from among various well-known and commercially-available programmers which would be suitable for the purposes of practicing the present invention. In the presently preferred embodiment of the invention, programmer 11 is the Medtronic 9760.

The activity exercise test in accordance with the presently disclosed embodiment of the invention is accomplished through a number of instructional screens displayed on programmer screen 55. The pacemaker is programmed such that the available data memory will be divided into a plurality of areas. One area collects the heart rate (i.e., bin number), percent paced, and sensor detects data at two-second intervals, as previously described. Another area collects the bin number, AV interval, and AS-to-VS/AP-to-VS data after each cardiac cycle, as previously described.

After the patient has exercised and the data is interrogated (i.e., retrieved from pacemaker 10 and stored in programmer memory), the heart rate and percent paced data is displayed in the trend format depicted in FIG. 6. The sensor detects data is recalculated using the same algorithms used by pacemaker 10 itself, and displayed as the projected activity rate. Initially, pacemaker 10 will preferably calculate the projected activity rate according to the parameters actually programmed into pacemaker 10. However, in accordance with one aspect of the present invention, the physician may change the rate-response settings and cause the projected activity rate to be recalculated using the changed settings. Thus, the physician can observe the effects that the hypothetical settings have on the actual patient exercise data. If the physician determines that the hypothetical settings are preferable to the currently programmed settings, there is the opportunity for the new settings to be programmed into pacemaker 10 from the screen shown in FIG. 6.

In the programmer screen depicted in FIG. 6, a parameter control area designated generally as 180 displays the pacemaker parameter settings, including the Activity Threshold Setting, Acceleration, Deceleration, Lower Rate, Upper Activity Rate, and Rate Response Setting. As previously noted, the values initially displayed in parameter area 180 are those currently programmed into pacemaker 10; the currently programmed values are determined through interrogation of pacemaker 10 upon initiation of the activity exercise test in accordance with the presently disclosed embodiment of the invention. Also in parameter area 180 are a plurality of parameter control "buttons" 182, 184, 186, 188, 190, 192, 194, 196, 198, and 200. As previously noted, programmer 11 preferably has a touch-sensitive screen such that the various buttons displayed thereon can be actuated by means of stylus 56 or the like. Thus, for example, if the physician desires to increase the rate-response Acceleration setting, this is accomplished by touching programmer screen 55 at the area of button 194; decreasing the Lower Rate setting is accomplished by touching screen 55 in the area of button 192, and so on.

Also displayed in parameter area 180 is the Max(imum) Achieved Rate, which reflects the maximum pacing rate that was attained by pacemaker 10 during the exercise test with the settings displayed in parameter area 180. A parameter called Desired Rate is controllable by means of buttons 182 and 184. Desired Rate is selected by the physician based upon his or her assessment of what pacing rate should be attained by pacemaker 10 given the exercise actually performed by the patient during the test. Changing the Desired Rate using buttons 182 and 184 has the effect of changing the Rate Response setting, which is also displayed in parameter area 180 but which is not itself directly adjustable on the screen of FIG. 6.

On the left-hand side of the programmer screen depicted in FIG. 6 is a data display area 202. Data display area 202 includes a graph of rate (in pulses per minute, along the vertical axis) versus time (in minutes, along the horizontal axis). A horizontal line 204 (UAR) represents the Upper Activity Rate setting displayed in parameter area 180. A horizontal line 206 (DR) represents the Desired Rate setting displayed in parameter area 180. A horizontal line 208 (LR) represents the Lower Rate Setting displayed in parameter area 180.

A dashed line 210 in data display area 202 represents the computed activity rate of pacemaker 10 given the activity performed by the patient during the test and the parameter settings displayed in parameter area 180. The activity rate represented by line 210 is computed according to the same algorithm used by pacemaker 10. Thus, if the parameters displayed in parameter area 180 are the same as those actually programmed into pacemaker 10, the activity rate represented by line 210 will reflect the actual pacing rate of pacemaker 10 during the patient's exercise. However, after the test, the physician can adjust the settings in parameter area 180 and the activity rate represented by line 210 will be recomputed, using the same algorithm but with the adjusted settings. This allows the physician to observe the effects of different settings before actually programming such settings into pacemaker 10.

Also displayed in data display area 202 are a plurality of boxes, such as those designated by reference numerals 212, 214, 216, and 218 in FIG. 6. Each of the boxes represents a bin value. In the presently preferred embodiment, each box is seven pixels wide. Therefore, if the exercise test is performed for two minutes or less, each box represents a single two-second interval. If the exercise test is performed for two to four minutes, each box represents an average of two two-second samples. Similarly, if the test is performed for four to six minutes, each box represents an average of three two-second interval values. For the projected activity sensor rate data, if the test is performed for two minutes or less, the projected sensor rate data is plotted in the center of each box. If the test is performed for two to four minutes, every other projected sensor rate data is plotted at the center of each box, and if the test is performed for four to six minutes, every third projected sensor rate data is plotted at the center of each box. The height and vertical position of each box represents a range of rates, i.e., the displayed rate range for a bin, as set forth in Table 2 above.

For example, the box designated 212 in FIG. 6 represents a bin value of 28, which according to Table 2 corresponds to a rate range of between 60.47 and 64.00 beats per minute (BPM). Thus, box 212 indicates that during the two-second time interval corresponding to box 212, the patient's heart rate was in the range between 60.47 and 64.00 BPM. Likewise, box 214 is at a vertical position corresponding to a bin value of 24, indicating that during the two-second time interval corresponding to the horizontal position of box 214, the patient's heart rate was in the range between 80.84 and 83.48 BPM.

As shown in FIG. 6, boxes such as 212, 214 and 216 are different shades. A legend designated as 220 in data display area 202 identifies the meaning of the different shades of the boxes. In particular, a white box, such as box 212, indicates that during the two-second interval corresponding to that box, the percentage of paced events was between zero and ten percent. A gray box, such as boxes 214 and 218, indicates that during the two-second time interval corresponding to such a box the percentage of paced events was between 11% and 89%. Finally, a black box, such as box 216 in FIG. 6, indicates that during the two-second interval corresponding to that box, the percentage of paced events was between 90% and 100%.

In the particular case illustrated in the data display area in FIG. 6, therefore, it can be seen that as the patient's heart rate increased, an increasing percentage of paced events occurred. This behavior is typical of one form of a common condition called chronotropic incompetence.

In FIG. 6, only three different shades of boxes, representing three percent paced ranges, are used. This is due mainly to the limited resolution of display screen 55. Recall from Table 1, however, that seven ranges of percent paced data are developed by the percent paced algorithm of FIG. 4. Therefore, it is contemplated by the inventors that if higher resolution were available on the programmer's screen, as many as seven different shades of boxes could be displayed, giving the physician an even better indication of percentage of paced events throughout the course of the patient's exercise.

As would be appreciated by those of ordinary skill in the art, the display depicted in FIG. 6 presents a considerable amount of information regarding the operation of and interaction between the patient's heart and pacemaker, including the percentage of paced events, the patient's actual heart rate, and the pacemaker's pacing rate. The information is presented in an advantageous way that is believed to be readily understandable and effective in showing the effects of different parameter settings on the operation of both the pacemaker and the patient.

Figure 7:
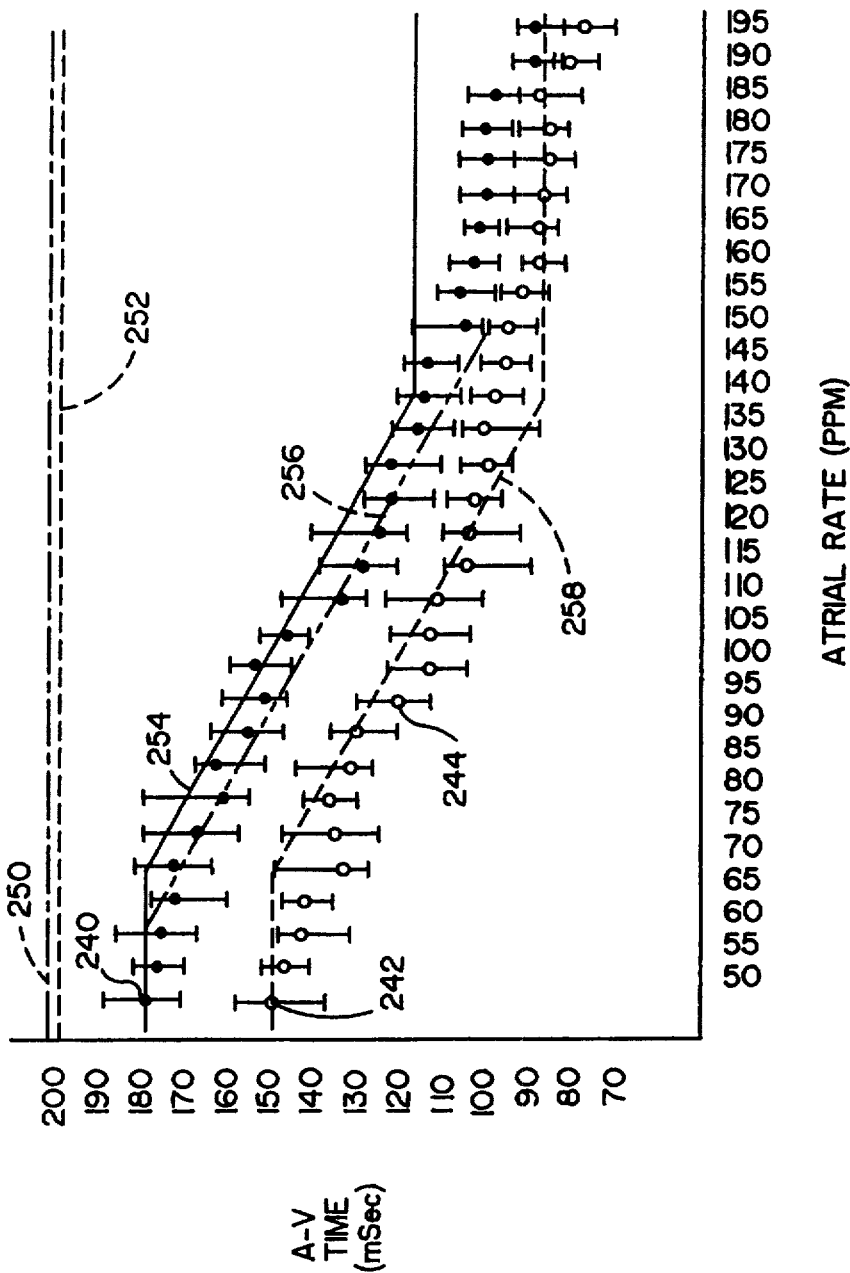
FIG. 7 is an illustration of another programmer display screen in accordance with the disclosed embodiment of the invention.

Turning now to FIG. 7, there is shown another programmer screen that is used to display the AV interval data collected at the end of each cardiac cycle during the patient's exercise. The screen of FIG. 7 is used to display the bin and AV data obtained at the end of each cardiac cycle, as previously described.

As set forth in the legend in the screen of FIG. 7, several parameters are plotted therein. A first line, designated with reference numeral 250, shows that the AP-to-VP interval is temporarily programmed to a high level, e.g., 200-mSec, during the exercise test. Similarly, as shown by the line designated with reference numeral 252, the AS-to-VP interval is temporarily programmed to a high value during the exercise test. A line designated with reference numeral 254 indicates the programmed AP-to-VP interval profile (i.e., the AP-to-VP profile programmed before initiating the exercise test), and a line designated with reference numeral 258 indicates the programmed AS-to-VP profile (i.e., the AS-to-VP profile programmed prior to initiating the exercise test). Finally, a line representing the AV profile of a typical healthy head is indicated with reference numeral 256.

As shown in FIG. 7, the AV data collected during the activity exercise test in accordance with the presently disclosed embodiment of the invention is presented in two groups, one reflecting the AV interval durations for AP-to-VS cardiac cycles, the other reflecting the AV interval durations for AS-to-VS cardiac cycles. The data, after being communicated from pacemaker 10 to the external programmer, is sorted according to bin number and according to whether it represents AP-to-VS or AS-to-VS data. AP-to-VS data is displayed, for example, with solid data points such as the one designated by reference numeral 240, so as to be distinguished from AS-to-VS data, which is displayed, for example, with hollow data points like the one designated with reference numeral 242 in FIG. 7.

Each data point in FIG. 7 corresponds to one of the 32 bins identified in Table 2 above. The range of AV interval durations associated with each data point indicates the maximum and minimum AV interval durations for that bin; the data point itself represents the mean of all AV interval durations in the bin. Thus, for example, data point 244 and the range associated therewith is associated with bin 22, and reflects the fact that during the patient's exercise test, the cardiac cycles in the range of durations corresponding to bin 22 had a mean AS-to-VS AV interval duration of approximately 120-mSec, and had AV interval durations ranging from a maximum of approximately 130-mSec to a minimum of approximately 115-mSec.

FIG. 7 also indicates that, in accordance with the presently disclosed embodiment of the invention, the programmed AS-to-VP and AS-to-VS AV interval durations were set at a high level, specifically, 200-mSec.

The programmer interprets the measured pace-sense AV-offset (i.e., the difference between AS-to-VS AV intervals and AP-to-VS AV intervals), and suggests profiles for the pace and sense AV rate-adaptation. The physician can accept the programmer's suggestion, for example with a single touch of the touch-screen display, or modify the suggested profiles.

In accordance with another aspect of the present invention, pacemaker 10 includes programming in its memory for periodically automatically adjusting the AV rate-adaptation profiles, between patient follow-up visits to the physician. According to a preset schedule, pacemaker 10 occasionally lengthens the programmed AS-to-VP and AP-to-VP AV intervals, preferably at several different atrial rates between the programmed lower and upper rates, if possible. The pacemaker's software then uses a linear function-fitting algorithm to fit two linear profiles to the measurements of intrinsic AV conduction times. The pacemaker adjusts the profiles of the AS-to-VP and AP-to-VP intervals such that intrinsic conduction will be allowed to occur if it can, and ventricular pacing will occur where the intrinsic conduction either doesn't exist or is too slow.

A curve-fitting algorithm believed to be suitable for the purposes of enabling pacemaker 10 to fit an AV rate-adaptation profile to data obtained during the automatic adjustment just described is disclosed in Johnson, "Multidimensional Curve-Fitting Program for Biological Data", *Computer Programs in Biomedicine* 18 (1984), pp. 259–264, which is hereby incorporated by reference herein in its entirety.

From the foregoing detailed description of a particular embodiment of the invention, it should be apparent that a method and apparatus for achieving optimal rate-responsive pacemaker therapy has been disclosed. Although a specific embodiment of the invention has been described herein in some detail, it is to be understood that this description has been provided for the purposes of illustration only, and is not intended to be limiting with respect to the scope of the invention. It is contemplated that numerous alternative implementations, and various alterations, substitutions and modifications may be made to the embodiment described herein may be made without departing from the spirit and scope of the present invention as defined in the appended claims, which follow.

What is claimed is:

1. A rate-responsive pacemaker system, comprising an implantable pulse generator unit and an external programming unit, wherein said implantable pulse generator unit comprises:

pulse generator means for generating pacing pulses;
   sensing circuitry means for detecting electrical cardiac signals;
   sensor means for producing a sensor output signal reflecting a patient's metabolic demand for oxygenated blood;
   control means for controlling the rate of delivery of pacing pulses by said pulse generator means in accordance with said sensor output signal and further comprising means for inhibiting delivery of pacing pulses in the presence of normal electrical cardiac signals;
   memory means for storing numeric data;
   processing means coupled to said control means and to said memory means, for computing and storing in said memory means, data reflecting percentages of paced cardiac events occurring during each one of a succession of predefined intervals, and further comprising means for storing in said memory means, data reflecting said sensor output signal during each one of said succession of predefined intervals, data reflecting heart rate during each one of said succession of predefined intervals, and data reflecting AV interval durations of each one of a succession of cardiac cycles;
   first telemetry circuit means, coupled to said memory means and to said control means, responsive to an interrogate signal from said external programming unit for transmitting said percentage of paced events data, said sensor output signal data, said heart rate data, and said AV interval data to said external programming unit;

and wherein said external programming unit comprises:

a second telemetry circuit means for sending said interrogate signal and for receiving said data transmitted by said first telemetry circuit means and;

means for displaying said percentage of paced events data, said heart rate data, sensor signal data, and said AV interval data.

2. A pacemaker system in accordance with claim 1, wherein said sensing circuitry means comprises means for sensing atrial electrical signals, and wherein said pulse generator means comprises means for generating ventricular pacing pulses, and wherein said control means comprises means responsive to a sensed atrial signal for triggering generation of a ventricular pacing pulse after a defined AV interval which varies as a function of said sensor output signal.

3. A pacemaker system in accordance with claim 1, wherein said control means comprises means for selecting from among a plurality of predefined functions relating said sensor output signal to said pacing rate.

4. A pacemaker system in accordance with claim 1, wherein said processing means comprises means for storing a bin number corresponding to a range of heart rates.

5. A pacemaker system in accordance with claim 4, wherein said processing means comprises means for storing a percent paced value corresponding to a range of percentages.

6. A pacemaker system in accordance with claim 5, wherein said display means comprises means for displaying said percentage of paced events data and said heart rate data in the form of a horizontal succession of boxes, where each box corresponds to a separate one of said succession of predefined time intervals and where each box's vertical position on said display screen corresponds to said bin number for the predefined interval corresponding to said box, and where each box is shaded according to said percent paced value for the predefined interval corresponding to said box.

7. A pacemaker system in accordance with claim 1, wherein said display means comprises means for displaying said percentage of paced events data and said heart rate data in the form of a horizontal succession of boxes, where each box corresponds to a separate one of said succession of predefined time intervals and where each box's vertical position on said display screen corresponds to said heart rate data for the predefined interval corresponding to said box, and where each box is shaded according to said percentage of paced events data for the predefined interval corresponding to said box.

8. A pacemaker system in accordance with claim 1, said processing means further comprises means for storing in conjunction with said AV interval data for each cardiac cycle an identification of whether an atrial pacing pulse was delivered for said cycle.

9. A pacemaker system in accordance with claim 1, wherein said sensing means comprises means for detecting atrial signals, and wherein said pulse generator means comprises means for generating ventricular pacing pulses, and wherein said control means further comprises means for triggering generation of ventricular pacing pulses after a defined AV interval has elapsed following detection of an atrial signal, means responsive to said sensor output signal for varying said defined AV interval in accordance therewith.

10. A method of monitoring and pacing a patient's heart comprising the steps of:

(a) sensing electrical cardiac signals of said patient's heart;

(b) producing an activity signal reflecting said patient's metabolic demand for oxygenated blood;

(c) delivering pacing pulses to said patient's heart at a base pacing rate when no electrical cardiac signals are sensed in step (a) above;

(d) determining said base pacing rate in accordance with a first function of said activity signal;

(e) inhibiting delivery of pacing pulses when normal electrical cardiac signals are sensed;

(f) defining a succession of intervals during a brief patient exercise;

(g) after each one of said succession of intervals, storing data reflecting percentages of paced cardiac events occurring during each said one of said succession of intervals;

(h) after each one of said succession of intervals, storing data reflecting said activity signal during each said one of said succession of intervals;

(i) during each one of said succession of intervals, measuring the duration of at least one cardiac cycle during said each one interval;

(j) after each one of said succession of intervals, storing heart rate data reflecting said duration of at least one cardiac cycle measured in step (i) above;

(k) during said succession of intervals, timing the duration of an AV interval of each cardiac cycle;

(l) after each cardiac cycle during said succession of intervals, storing data reflecting said AV interval duration of said cardiac cycle;

(m) after said succession of intervals displaying said percentage of paced events data, said heart rate data, sensor signal data, and said AV interval data.

11. A method in accordance with claim 10, wherein said step (a) of sensing electrical cardiac signals comprises sensing atrial electrical signals and wherein said method further comprises the steps of:

(o) delivering a ventricular pacing pulse following a defined AV interval initiated after sensing an atrial signal; and (p) varying said defined AV interval of step (o) above as a second function of said activity signal.

12. A method in accordance with claim 11, further comprising the steps of:

(r) periodically increasing said defined AV interval to a high value;

(s) detecting whether an ventricular signal occurs following a sensed atrial signal;

(t) when ventricular signal is found to occur in step (s), storing AV interval data reflecting time between said sensed atrial signal and said ventricular signal;

(u) storing, along with said AV interval data in step (t), data reflecting said patient's current activity level;

(v) repeating steps (r) through (u) above for different current activity levels;

(w) programming said second function in accordance with said stored activity level data and said stored AV interval data.

13. A method in accordance with claim 10, further comprising the step of:

(q) selecting said first function of said activity signal from among a plurality of predefined functions.

14. A method in accordance with claim 10, wherein said step (j) of storing heart rate data comprises the steps of selecting a bin number corresponding to a range of heart rates, as a function of said measured cardiac cycle duration, and storing said bin number.

15. A method in accordance with claim 14, wherein said step (g) of storing percentage of paced events data comprises the sub-step of computing a percent paced value corresponding to a range of percentages.

16. A method in accordance with claim 10, wherein said step (l) of storing AV interval data for each cardiac cycle includes the step of storing an identification of whether an atrial pacing pulse was delivered for each said cycle.

17. A method in accordance with claim 10, wherein said step (e) of defining a succession of intervals comprises defining a succession of two-second intervals.

18. A method in accordance with claim 10, wherein said step (e) of defining a succession of intervals comprises defining a succession of four-second intervals.

19. A method of monitoring and pacing a patient's heart, comprising the steps of:
(a) causing said patient to engage in an exercise during an exercise period;
(b) defining a plurality of successive time intervals during said exercise period;
(c) after each one of said plurality of time intervals, recording heart rate data reflecting said patient's heart rate during said time interval;
(d) after each one of said plurality of time intervals, recording percent paced data reflecting a percentage of paced events during said time interval;
(e) after each one of said plurality of time intervals, recording activity data reflecting a level of patient activity during said time interval;
(f) after each cardiac cycle during said exercise period, recording AV interval data reflecting a duration of an AV interval of said cardiac cycle;
(g) after each cardiac cycle during said exercise period, recording pace/sense data reflecting whether an atrial stimulating pulse was delivered during said cardiac cycle;
(h) after said exercise period, simultaneously displaying said heart rate data, said percent paced data, and activity data; and
(i) after said exercise period, displaying said AV interval data and said pace/sense data.

20. A pacemaker system, comprising an implantable pacemaker and an external monitoring unit;
wherein said implantable pacemaker comprises:
pulse generator means for generating pacing pulses at a pacing rate;
sensing means for sensing atrial and ventricular signals;
control means, coupled to said pulse generator means, for controlling said pacing rate;
memory means for storing numeric data;
computing means coupled to said sensing means, said control means and to said memory means, for simultaneously computing and storing in said memory means, data reflecting a patient's heart rate and data reflecting AV interval durations of each one of a succession of cardiac cycles; and
a first telemetry circuit, coupled to said memory means and to said control circuit, said first telemetry circuit comprising means responsive to an interrogate signal from said external programming unit, for transmitting said heart rate data and said AV interval data to said external programming unit; and wherein said external monitoring unit comprises:
a second telemetry circuit comprising means for sending said interrogate signal and means for receiving said data transmitted by said first telemetry transmitter circuit; and
means for displaying said heart rate data versus said AV interval data.

21. A pacemaker system in accordance with claim 20, further comprising:
sensor means, coupled to said control means, for producing an output signal reflecting a patient's metabolic demand for oxygenated blood; and
wherein said control means comprises means for varying said pacing rate as a function of said output signal.

22. A pacemaker system in accordance with claim 21, wherein said control means comprises means responsive to a sensed atrial signal for delivering a ventricular pacing pulse after a defined AV interval which varies as a function of said output signal.

23. A pacemaker system in accordance with claim 20, wherein said computing means comprises means for selecting a bin number corresponding to a range of heart rates and means for storing said bin number in said memory means.

24. A pacemaker system in accordance with claim 20, wherein said pulse generator means comprises means for generating atrial pacing pulses and wherein said computing means comprises means for storing in said memory means an indication of whether an atrial pacing pulse was delivered, in each said cardiac cycle.

25. A pacemaker system in accordance with claim 20, wherein said pulse generator means comprises means for generating ventricular pacing pulses and wherein said computing means comprises means for storing in said memory means an indication of whether a ventricular pacing pulse was delivered, in each said cardiac cycle.

26. A pacemaker system in accordance with claim 20, wherein said computing means comprises means for storing in said memory means an indication of whether an atrial signal was sensed, in each said cardiac cycle.

27. A pacemaker system in accordance with claim 20, wherein said computing means comprises means for storing in said memory means an indication of whether a ventricular signal was sensed, in each said cardiac cycle.

28. A method of monitoring and pacing a patient's heart, said method comprising the steps of:
implanting a pacemaker having the capability to sense atrial and ventricular signals and to deliver pacing pulses, in said patient;
causing said patient to engage in an exercise during an exercise period;
defining a plurality of successive time intervals during said exercise period;
after each one of said plurality of time intervals, recording activity data reflecting a level of patient activity during said time interval;
after each cardiac cycle during said exercise period, recording AV interval data reflecting a duration of an AV interval of each said cardiac cycle;
after each cardiac cycle during said exercise period, recording pace/sense data reflecting whether a stimulating pulse was delivered during said cardiac cycle; and
after said exercise period, simultaneously displaying said activity data, said AV interval data and said pace/sense data.

* * * * *